United States Patent
Smith et al.

(10) Patent No.: US 7,903,906 B2
(45) Date of Patent: Mar. 8, 2011

(54) OPTICAL SENSING DEVICES AND METHODS

(75) Inventors: Terry L. Smith, Roseville, MN (US); Barry J. Koch, Woodbury, MN (US); Yasha Yi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1103 days.

(21) Appl. No.: 11/617,932

(22) Filed: Dec. 29, 2006

(65) Prior Publication Data

US 2009/0310902 A1    Dec. 17, 2009

Related U.S. Application Data

(63) Continuation-in-part of application No. 11/616,338, filed on Dec. 27, 2006, now Pat. No. 7,486,855, and a continuation-in-part of application No. 11/565,955, filed on Dec. 1, 2006, now Pat. No. 7,512,298, and a continuation-in-part of application No. 11/565,920, filed on Dec. 1, 2006, and a continuation-in-part of application No. 11/565,935, filed on Dec. 1, 2006, now Pat. No. 7,702,202.

(51) Int. Cl.
*G02B 6/26* (2006.01)

(52) U.S. Cl. .......................................................... 385/12

(58) Field of Classification Search .................. None
See application file for complete search history.

(56) References Cited

U.S. PATENT DOCUMENTS

| | | | |
|---|---|---|---|
| 4,185,257 A | 1/1980 | Nakajima | |
| 4,775,214 A | 10/1988 | Johnson | |
| 5,398,256 A | 3/1995 | Hohimer et al. | |
| 5,420,880 A | 5/1995 | Tabatabaie et al. | |
| 5,537,432 A | 7/1996 | Mehuys et al. | |
| 5,651,018 A | 7/1997 | Mehuys et al. | |
| 5,748,663 A | 5/1998 | Chenausky | |

(Continued)

FOREIGN PATENT DOCUMENTS

WO    WO 98/53535    11/1998

(Continued)

OTHER PUBLICATIONS

U.S. Appl. No. 11/277,769, filed Mar. 29, 2006, entitled "Coupling Light Into Microresonators."

(Continued)

*Primary Examiner* — Tina M Wong
(74) *Attorney, Agent, or Firm* — Kristofor L. Storvick

(57) ABSTRACT

An optical sensing system and method of using it includes a light source and a first bus waveguide having an input port that is in optical communication with the light source. The system further includes a microresonator configured so that the light source excites at least first and second resonant guided optical modes of the microresonator. The microresonator includes a first location on a surface of a core of the microresonator where a field intensity of the first mode is greater than a field intensity of the second mode. The microresonator core has a first cladding at the first location. The microresonator also has a second location on a surface of the core of the microresonator where a field intensity of the first mode is less than or equal to a field intensity of the second mode, the microresonator core having a second cladding at the second location. The first cladding is different than the second cladding.

15 Claims, 16 Drawing Sheets

U.S. PATENT DOCUMENTS

| | | | |
|---|---|---|---|
| 5,910,963 | A | 6/1999 | Simon |
| 6,009,115 | A | 12/1999 | Ho |
| 6,286,262 | B1 | 9/2001 | Prevot et al. |
| 6,490,039 | B2 * | 12/2002 | Maleki et al. .................. 356/436 |
| 6,515,749 | B2 | 2/2003 | Pipino |
| 6,580,851 | B1 | 6/2003 | Vahala et al. |
| 6,583,399 | B1 | 6/2003 | Hunziker et al. |
| 6,608,716 | B1 | 8/2003 | Armstrong et al. |
| 6,657,731 | B2 | 12/2003 | Tapalian et al. |
| 6,661,950 | B1 | 12/2003 | Strecker |
| 6,680,962 | B2 | 1/2004 | Liu et al. |
| 6,711,200 | B1 | 3/2004 | Scherer et al. |
| 6,741,628 | B2 | 5/2004 | Painter et al. |
| 6,751,368 | B2 | 6/2004 | Lim et al. |
| 6,772,480 | B2 | 8/2004 | Prevot et al. |
| 6,781,690 | B2 | 8/2004 | Armstrong et al. |
| 6,795,481 | B2 | 9/2004 | Maleki et al. |
| 6,876,796 | B2 | 4/2005 | Garito et al. |
| 6,888,987 | B2 | 5/2005 | Sercel et al. |
| 6,901,101 | B2 | 5/2005 | Frick |
| 6,947,632 | B2 | 9/2005 | Fischer et al. |
| 7,062,131 | B2 | 6/2006 | Ilchenko |
| 7,085,452 | B1 | 8/2006 | Lin et al. |
| 7,228,016 | B2 * | 6/2007 | Beausoleil ..................... 385/12 |
| 7,271,379 | B2 | 9/2007 | Fan et al. |
| 7,292,112 | B2 | 11/2007 | Oxborrow |
| 7,665,891 | B1 | 2/2010 | Savchenkov et al. |
| 2002/0122179 | A1 | 9/2002 | Pipino |
| 2003/0063426 | A1 | 4/2003 | Smirnov et al. |
| 2003/0202555 | A1 | 10/2003 | Liu et al. |
| 2003/0231826 | A1 | 12/2003 | Boyd et al. |
| 2004/0023396 | A1 | 2/2004 | Boyd et al. |
| 2004/0137478 | A1 | 7/2004 | Arnold et al. |
| 2004/0247008 | A1 | 12/2004 | Scheuer et al. |
| 2005/0003520 | A1 | 1/2005 | Misiakos et al. |
| 2005/0013529 | A1 | 1/2005 | Chiu et al. |
| 2005/0018274 | A1 | 1/2005 | Halas et al. |
| 2005/0077513 | A1 | 4/2005 | Fan et al. |
| 2005/0078731 | A1 | 4/2005 | Fan et al. |
| 2005/0141809 | A1 | 6/2005 | Gardner et al. |
| 2005/0210989 | A1 | 9/2005 | Ja et al. |
| 2005/0226564 | A1 | 10/2005 | Gardner et al. |
| 2005/0263679 | A1 | 12/2005 | Fan et al. |
| 2005/0286602 | A1 | 12/2005 | Gunn et al. |
| 2006/0062508 | A1 | 3/2006 | Guo et al. |
| 2006/0170931 | A1 | 8/2006 | Guo et al. |
| 2007/0001773 | A1 | 1/2007 | Oxborrow |
| 2007/0147445 | A1 | 6/2007 | Ishaaya et al. |

FOREIGN PATENT DOCUMENTS

| | | |
|---|---|---|
| WO | WO 01/40757 | 6/2001 |
| WO | WO 2005/116615 | 12/2005 |

OTHER PUBLICATIONS

U.S. Appl. No. 11/565,920, filed on Dec. 1, 2006, entitled "Optical Sensing Device."

U.S. Appl. No. 11/565,955, filed Dec. 1, 2006 entitled "Optical Sensing Methods."

U.S. Appl. No. 11/565,935, filed on Dec. 1, 2006, entitled "Optical Microresonator."

U.S. Appl. No. 11/617,923, filed on Dec. 29, 2006, entitled "Optical Sensing Devices and Methods."

U.S. Appl. No. 11/616,338, filed on Dec. 27, 2006, entitled "Optical Microresonator."

Brun et al., "Coupling nanocrystals to a high-Q silica microsphere: Entanglement in quantum dots via photon exchange," *Physical Review A*, vol. 61, pp. 032307-1-5 (2000).

Fan et al., "Coupling semiconductor nanocrystals to a fused-silica microsphere: a quantum-dot microcavity with extremely high Q factors," *Optics Letters*, vol. 25, No. 21 pp. 1600-1602 (Nov. 1, 2000).

Fano, "Effects of Configuration Interaction on Intensities and Phase Shifts," *Physical Review*, vol. 124, No. 6, pp. 1866-1878 (Dec. 15, 1961).

Götzinger et al., "Towards controlled coupling between a high-Q whispering-gallery mode and a single nanoparticle," *Appl. Phys. B*, vol. 73, pp. 825-828 (2001).

Little et al., "Second-order filtering and sensing with partially coupled traveling waves in a single resonator", *Optics Letters*, vol. 23, No. 20, pp. 1570-1572 (Oct. 15, 1998).

Soller et al., "Dynamic modifications to the plasmon resonance of a metallic nanoparticle coupled to a planar waveguide: beyond the point-dipole limit," *J. Opt. Soc. Am. B.*, vol. 19, No. 5, pp. 1195-1203 (May 2002).

Xu, et al., "Scattering-theory analysis of waveguide-resonator coupling," *Physical Review E*, vol. 62, No. 5, pp. 7389-7404 (Nov. 2000).

* cited by examiner

OPTICAL SENSING DEVICES AND METHODS

REFERENCE TO RELATED APPLICATIONS

This application is a continuation-in-part of four commonly-assigned patent applications: OPTICAL SENSING METHODS, having application Ser. No. 11/565,955, filed on Dec. 1, 2006; OPTICAL SENSING DEVICE, having application Ser. No. 11/565,920, filed on Dec. 1, 2006; OPTICAL MICRORESONATOR, having application Ser. No. 11/565,935, filed on Dec. 1, 2006; and OPTICAL MICRORESONATOR, having application Ser. No. 11/616,338, filed on Dec. 27, 2006. The entirety of these four patent applications are incorporated herein by reference.

This application is related to commonly-assigned patent application OPTICAL SENSING DEVICES AND METHODS, having application Ser. No. 11/617,923 filed on the same date herewith.

FIELD OF THE INVENTION

The invention is directed generally to optical devices, and more particularly to optical sensors that use microresonators.

BACKGROUND

Optical sensing is becoming an important technology for detection of biological, chemical, and gaseous species. Optical sensing may offer advantages of speed and sensitivity. In recent years, many novel photonic structures and materials have been developed to make very sensitive optical devices.

One optical sensing method for analyte detection uses integrated optical waveguides. Such sensors have been demonstrated to be able to detect chemical and biological species adsorbed onto the waveguide surface. But integrated optical waveguide chemical analysis can require a large sensing device (typically several centimeters long) in order to obtain sufficient optical signal change for many analytical applications.

Surface plasmon resonance (SPR) has also been used to make optical sensors. SPR technology has been commercialized and it has become an essential tool to characterize and quantify biomolecular interactions. But such measurement systems can be bulky.

Optical microresonators are currently under intensive investigation for applications in biochemical, chemical, and gas sensing. Optical microresonators are very small devices that can have high quality factors (Q-factor) where Q-factor commonly refers to the ratio of a resonant wavelength to a resonance linewidth. For example, microresonators made of glass spheres can be used to make very sensitive optical sensors since the light trapped in the microsphere resonator circulates many times producing a device with a high Q-factor ($>10^6$) which allows effective enhancement of the optical interaction between an analyte on the surface of the microsphere and the light circulating in the resonator. In an optical microresonator sensor a bus waveguide is used to excite guided optical modes located close to the surface of the microresonator. One example of resonant optical modes is a whispering gallery mode. An analyte is then located within the evanescent field of the modes of the microsphere. The change in refractive index of the sensor is detected by a shift in the resonant frequencies. The shifted spectra can be extracted from the microresonator using a second bus waveguide that is connected to a detector.

A variety of types of optical microresonators have been investigated for the purpose of making optical sensors, but microspheres, microrings, and microdisks have received the most attention. Microdisks or microrings based on semiconductor fabrication processes are relatively easy to fabricate in a large quantity and/or high density. Their positions with respect to waveguides can be adjusted using fabrication technologies such as dry/wet etching and layer deposition. The Q-factors of these resonators, however, are typically below $10^4$, due at least in part to the surface roughness and to material absorption.

In the conventional approach to sensing using microspheres, bonding of an analyte to the surface of the sphere results in a small change in the effective refractive index of the sphere. This results in a small shift of the wavelength position of the peaks in the resonance spectrum. These shifts are typically in the picometer range. In order to detect such small shifts expensive equipment for spectral analysis is required. Furthermore, the microresonator must be designed to give a very narrow linewidth so that the small peak shifts can be detected. This requires a high finesse (free spectral range divided by linewidth), or equivalently, high quality factor (operating wavelength divided by linewidth) microresonator. This translates to the need for low loss waveguides in the microresonator and weak coupling between the microresonator and the bus waveguide in order to detect the small frequency shift.

In order to detect the small change in wavelength due to detection of an analyte, other mechanisms that can produce wavelength shifts need to be controlled or compensated. In particular, wavelength shifts due to the temperature dependencies of the refractive indices of the materials that make up the resonator must be understood and not confused with detection signals.

There is a need for improved optical sensing systems that use microresonators.

SUMMARY OF THE INVENTION

Generally, the present invention relates to optical systems. The present invention also relates to optical sensors that include one or more microresonators.

In one embodiment of the present invention, an optical sensing system includes a light source and one or more bus waveguides including a first bus waveguide. The first bus waveguide includes an input port that is in optical communication with the light source. The system further includes a microresonator configured so that the light source excites at least first and second resonant guided optical modes of the microresonator. The microresonator includes a first location on a surface of a core of the microresonator where a field intensity of the first mode is greater than a field intensity of the second mode, the microresonator core having a first cladding at the first location, and a second location on a surface of the core of the microresonator where a field intensity of the first mode is less than or equal to a field intensity of the second mode, the microresonator core having a second cladding at the second location. The first cladding is different than the second cladding.

In another embodiment of the invention, an optical sensing system includes a light source and one or more bus waveguides including a first bus waveguide. The first bus waveguide includes an input port that is in optical communication with the light source. The system further includes a microresonator comprising a surface, wherein the microresonator is configured so that the light source excites at least first and second resonant guided optical modes of the microresonator. The microresonator surface further includes an unavailable first portion configured to not permit the first and second modes to interact with a perturbation of the microresonator at the unavailable first portion. The microresonator surface further includes an available second portion different from the unavailable first portion, wherein the available second portion is configured to permit the first and second modes to interact with the perturbation of the microresonator in a way that the first and second resonant guided optical modes interact differently with the perturbation. In another embodiment, a method of detecting the presence of a perturbation of a microresonator includes providing an optical sensing system, where the system has a light source, one or more bus waveguides, the one or more bus waveguides comprising a first bus waveguide that has an input port that is in optical communication with the light source, and a microresonator comprising a surface and being optically coupled to the one or more bus waveguides. The microresonator is configured to support at least first and second resonant guided optical modes of the microresonator when the first and second modes are excited by the light source. The microresonator surface further includes an unavailable first portion configured to not permit the first and second modes to interact with a perturbation of the microresonator at the unavailable first portion. The method further includes the steps of exciting at least first and second resonant guided optical modes of the microresonator with the light source, exposing an available second portion of the surface of the microresonator to a perturbation of the microresonator, wherein the available second portion is different from the unavailable first portion, thereby causing the perturbation to interact differently with the first and second resonant guided optical modes, and detecting the interaction.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
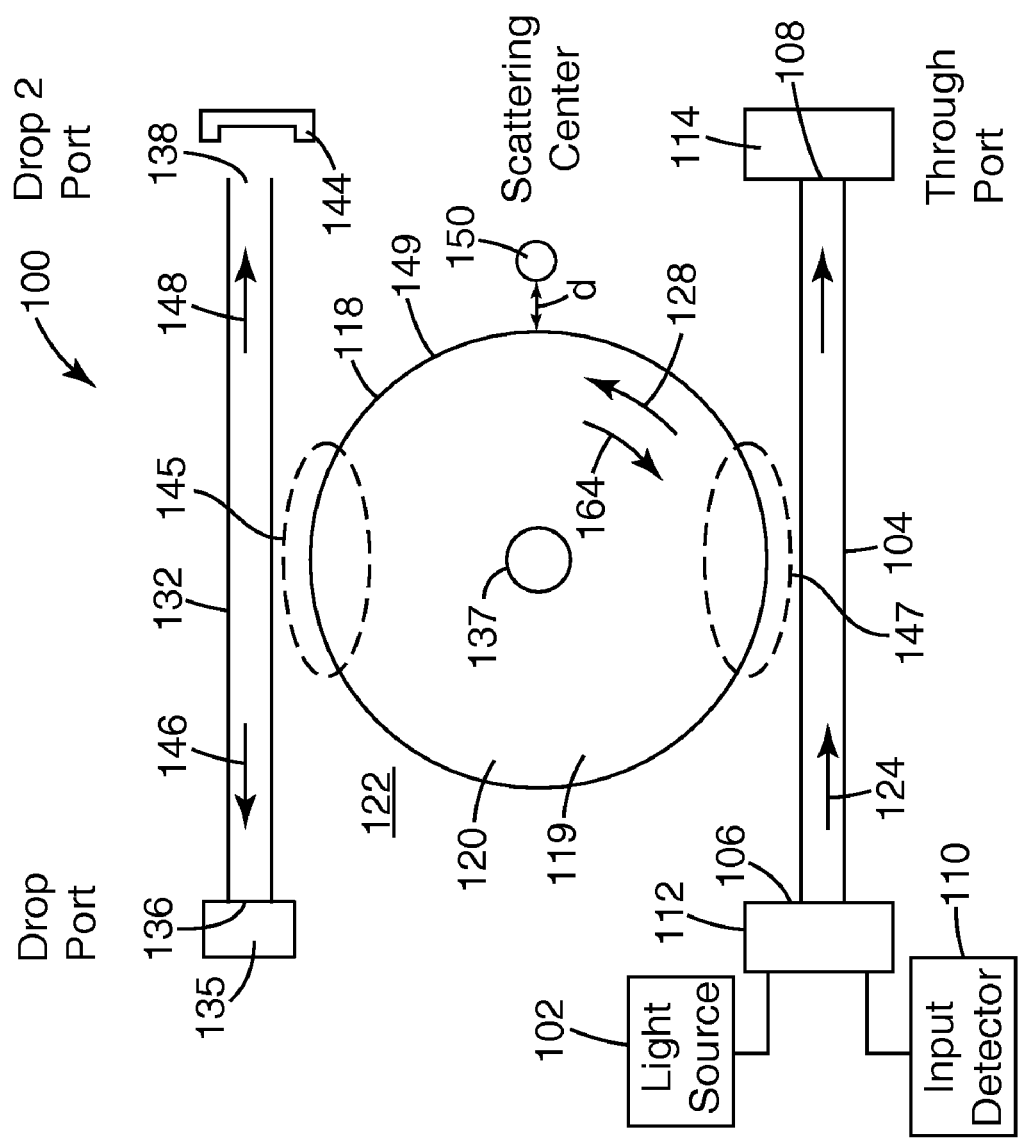
FIGS. 1, 2 and 3 are respective schematic top- and side-views of an optical system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention relates to an optical sensor that includes a waveguide, an optically resonant microcavity, and the capability of introducing a perturbation to the resonant guided optical modes of the microcavity. Such optically resonant microcavities may also be referred to as microresonators. As the term is used herein, a perturbation is a change of an optical characteristic of the microresonator. For example, a change in the refractive index of a surface or a portion of the microresonator, such as is caused by a coating on the surface of the microresonator or an optical coupling of the microresonator to a scattering center. Examples of scattering centers will be further described herein.

A new approach to optical sensing using microresonators is hereby presented in which the introduction or removal of a perturbation causes a shift in the wavelength characteristics of a signal. The perturbation is configured to differently affect a first guided optical mode and a second guided optical mode of the microresonator. For example, in some embodiments, the perturbation affects the first optical mode significantly and affects the second optical mode only negligibly or not at all. As a result, it is possible to screen out effects of other system changes that affect both the first and second guided optical modes. It is therefore possible to isolate the effect on the system of the introduction of the perturbation and more accurately determine the effect of the introduction of a perturbation. This approach is useful, for example, in reducing the effects of temperature-induced changes on the refractive indices of the core and cladding layers of the microresonator, which tend to affect the first and second optical modes in the same way.

In the specification, a same reference numeral used in multiple figures refers to the same or similar elements having the same or similar properties and functionalities.

An example of a microresonator-waveguide system 100 that uses a microresonator will now be described, as schematically illustrated in top view FIG. 1 and cross-sectional views FIGS. 2 and 3. As will be further discussed herein, systems with a single waveguide may also be used according to the invention. However, a double bus waveguide system will be discussed as the first example.

Optical device 100 includes an optical microresonator 118, a first optical waveguide 104, and a second optical waveguide 132 all disposed on a lower cladding layer 105 disposed on substrate 103.

Microresonator 118 is capable of quantizing the allowed optical modes of the microresonator into discrete modes by imposing one or more boundary conditions, such as one or more periodicity conditions. Microresonator 118 is capable of supporting at least two different guided optical modes such as first guided optical mode 128 and second guided optical mode 164, where guided optical mode 128 is different than guided optical mode 164, when the modes are excited by light source 102. In some cases, modes 128 and 164 have the same wavelength. In some cases, modes 128 and 164 have different wavelengths. If the modes 128 and 164 have substantially the same wavelengths, they may have different intensity levels for the wavelengths. As used herein, for a given optical configuration such as optical device 100, an optical mode refers to an allowed electromagnetic field in the optical configuration; radiation or radiation mode refers to an optical mode that is unconfined in the optical configuration; a guided mode refers to an optical mode that is confined in the optical configuration in at least one dimension due to the presence of a high index region; and a resonant mode refers to a guided mode that is subject to an additional boundary condition requirement in the optical configuration, where the additional requirement is typically periodic in nature.

Resonant modes are typically discrete guided modes. In some cases, a resonant mode can be capable of coupling to a radiation mode. In some other cases, a resonant mode can have a component that is radiation and not confined. In general, a guided mode of microresonator 118 can be a resonant or a non-resonant mode. For example, optical modes 128 and 164 can be resonant modes of microresonator 118.

In some cases, first guided optical mode 128 and/or second guided optical mode 164 is capable of propagating within the microresonator while maintaining a same electric field profile. In such cases, the shape or profile of the propagating mode remains substantially the same over time even if the mode gradually loses energy because of, for example, absorption or radiation losses.

Figure 2:
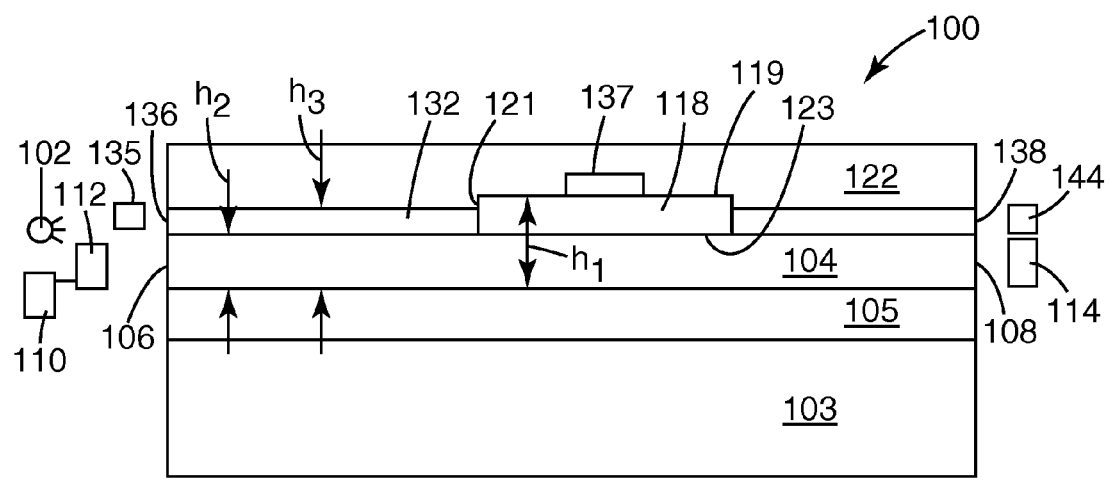
Figure 3:
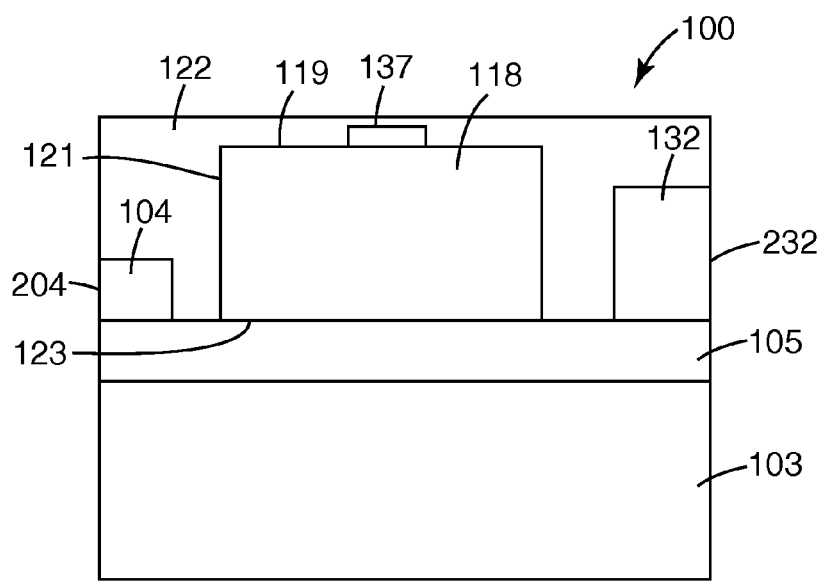

The microresonator 118 illustrated in FIGS. 1-3 is a disk microresonator, having a top planar surface 119, a bottom planar surface 123, and a cylindrical side surface 121. However, other microresonator configurations are used in other embodiments, as further discussed herein.

Referring to FIGS. 1-3, a light source 102 is in optical communication with the first bus waveguide 104. The end of the waveguide 104 where the light source is located is an input port 106. Another end of the waveguide 104 is the through port 108. An input port detector 110 is located at the input port 106. An optical component 112 is in optical communication with the light source 102, input detector 110, and input port 106 to allow input light 124 to communicate only with the input port 106, and allow light traveling toward the input port 106 in the first bus waveguide 104 to be directed toward the input detector 110. The optical component 112 is an optical splitter or optical circulator in certain embodiments. The input port detector 110 is in optical communication with the first bus waveguide 104, via the optical component 112, and is configured to detect light.

The microresonator 118 is capable of supporting at least first and second resonant optical modes 128 and 164, respectively, and in some embodiments is also capable of supporting other modes. The microresonator 118 is optically coupled to the first bus waveguide 104. Input port 106 is capable of optically coupling to both first and second resonant modes. Light 124 from the light source 102 is launched into the first bus waveguide 104 and propagates towards the through port 108. The microresonator 118 evanescently couples some of the light 124 out of the first bus waveguide 104, the out-coupled light propagates within the microresonator 118 at the resonant frequencies of the microresonator 118, such as first resonant optical mode 128 and second resonant optical mode 164. Microresonator 118 includes a core 120 and a cladding 122. In some embodiments, the upper cladding 122 can include water. In some cases, the upper cladding can include different materials, for example, at different locations. For example, some regions of the upper cladding can include water and some other regions of the upper cladding can include another material such as glass.

A second bus waveguide 132 is positioned in optical communication with the microresonator 118. A drop port 136 is located at one end of the second bus waveguide 132, while a drop 2 port 138 is located at another end of the second bus waveguide. The drop port 136 is capable of optically coupling to the first resonant optical mode. The drop 2 port 138 is not generally capable of optically coupling to the first resonant guided optical mode in the absence of a scattering center. A drop port detector 135 is located at the drop port 136. A drop 2 port detector 144 is located at the drop 2 port 138.

The microresonator 118 may be positioned in physical contact with, or very close to, the waveguides 104 and 132 so that a portion of the light propagating along the waveguides is coupled into the microresonator 118. Also, a portion of light propagating within the microresonator 118 will be coupled into the waveguides 104 and 132. Optical coupling is the transfer of optical energy from one core to the other. An optical coupling region is a region in space within which significant transfer of optical energy occurs. In FIG. 1, regions of the surface of the microresonator where optical coupling occurs between the resonator core and the cores of the waveguides 104 and 132 are referred to as coupling regions 145 and 147, respectively. In various embodiments, significant transfer of optical energy occurs where there is a transfer of about 1% or more of the coupled light energy, or about 5% or more.

Evanescent coupling is when the structure forming the optical core of the waveguide and structure forming the optical core of the resonator are not structurally joined to each other, so that optical coupling occurs primarily via overlap of the optical fields outside the cores of one or more of the structures. FIG. 1 is an example of a structure where evanescent coupling occurs. Core coupling is when the structure forming the optical core of the waveguide and structure forming the optical core of the resonator are structurally joined to each other, so that the optical coupling occurs primarily via overlap of the optical the optical fields inside the cores.

A center detector 137 is located on a surface of the microresonator at a center of one of the planar surfaces of the disk, such as the top surface 119 of the disk microresonator. In other embodiments, a center detector need not actually be attached at the center of the disk. Instead, an external detector is coupled to the center of the disk via a removable optical system. For example, an optical fiber could be put in contact with the center of the disk, or a lens system could be used to collect light from the center of the disk. In these embodiments, it may be advantageous to fabricate light extraction features, such as etched facets, on the center of the resonator to couple light out to the detector system.

FIG. 1 illustrates the location of five possible detectors. It is possible for an embodiment of the invention to include five detectors at each of the illustrated locations. However, it is more likely to have a single detector at one of the five possible locations, in various embodiments of the invention. Other embodiments of the invention have two, three or four detectors at each of the possible combinations of different detector locations.

FIG. 2 is a view of a cross-section through the first bus waveguide 104 and along an axis of the first bus waveguide. FIG. 3 is a view of a cross-section through the microresonator 118 and the two bus waveguides and perpendicular to an axis of the first bus waveguide. Each of the first and second optical waveguides has a core disposed between multiple claddings. For example, first optical waveguide 104 has a core having a thickness $h_2$ and disposed between upper cladding 122 and lower cladding 105. Similarly, second optical waveguide 132 has a core having a thickness $h_3$ disposed between upper cladding 122 and lower cladding 105. In some cases, upper cladding 122 can include air or water.

In the exemplary optical device 100 of FIGS. 1-3, microresonator 118 and optical waveguides 104 and 132 have different thicknesses. In general, thicknesses $h_1$, $h_2$, and $h_3$ may or may not have the same value. In some applications, microresonator 118 and optical waveguides 104 and 132 have the same thickness.

The impact of the introduction or removal of a perturbation, such as a scattering center, upon the microresonator system 100 is central to the method of the invention. As discussed above, a perturbation is a change of an optical characteristic of the microresonator. For example, a change in the refractive index of a surface or a portion of the surface of the microresonator, such as is caused by a coating on the surface of the microresonator, is an example of a perturbation. The optical coupling of the microresonator to a scattering center is another example of a perturbation. The use of a scattering center 150 as a perturbation is illustrated in FIG. 1 and will be described as an example of a perturbation, though other types of perturbation will also be described herein. However, before describing the use of a scattering center, the more conventional approach of relying on the effective index change produced directly by the bonding of a chemical analyte to the resonator surface will be described.

In one conventional approach to sensing using microresonators, a surface 149 of a core 120 of the microresonator 118 is functionalized to be capable of chemically specific bonding with an analyte. Bonding of an analyte to the surface of the microresonator causes a small change in the effective refractive index of the microresonator, which shifts the wavelength position of the peaks in the resonator transmission spectrum. These shifts are observed at the through port 108 and the drop port 136. Hence, the detection of a shift of the peaks of the transmission spectrum at the through port 108 and/or drop port 136 indicates the presence of an analyte. Other conventional approaches to sensing using microresonators exist, and some examples of various approaches are detailed in commonly-owned U.S. Published Patent Application 2006/0062508 which is incorporated herein by reference.

A new approach to optical sensing using microresonators is hereby presented which takes advantage of the fact that different optical modes have evanescent fields with different spatial characteristics. An evanescent field of an optical mode can interact with a perturbation only if the perturbation is located within the evanescent field. In one embodiment, a first optical mode has a field that is more available for interaction at the surface 149 or at certain locations on the surface 149 of the microresonator 118 than a field of a second optical mode. As a result, a perturbation at the microresonator surface 149 differently affects a first guided optical mode and a second guided optical mode of the microresonator.

For example, in some embodiments, the perturbation affects the first optical mode significantly and affects the second optical mode only negligibly or not at all. As a result, it is possible to screen out effects of other system changes that affect both the first and second guided optical modes. It is therefore possible to isolate the effect on the system of the introduction of the perturbation and more accurately determine the effect of the introduction of a perturbation.

For example, a change in the temperature of the system can cause a change in the refractive index of the microresonator core and surrounding cladding material. A change in the refractive indices of both the core and cladding material will typically produce a wavelength shift of both the first and second optical mode. In contrast, the coupling of a scattering center such as a nanoparticle to the microresonator, will differently affect the first and second modes. By determining the difference between the shift of the first optical mode and the shift of the second optical mode, the effect of a temperature change can be taken into account and eliminated from the determination of the effect of the scattering center on the first optical mode.

During a sensing event according to one embodiment of the present invention, first guided optical mode 128 and second guided optical mode 164 are excited in the microresonator 118 with the light source 102. Then, a perturbation is introduced to the optical system, which is a change of an optical characteristic of the microresonator such as a change in the refractive index of a surface or a portion of a surface of the microresonator. One example of a perturbation is where the strength of optical coupling between a scattering center and a microresonator is altered. This occurs by, for example, a scattering center becoming optically coupled to the microresonator, or by a scattering center being removed from optical coupling with the microresonator. When the scattering center is optically coupled to the microresonator, the optical fields of one or more of the resonator's modes overlap with the scattering center.

Figure 4:
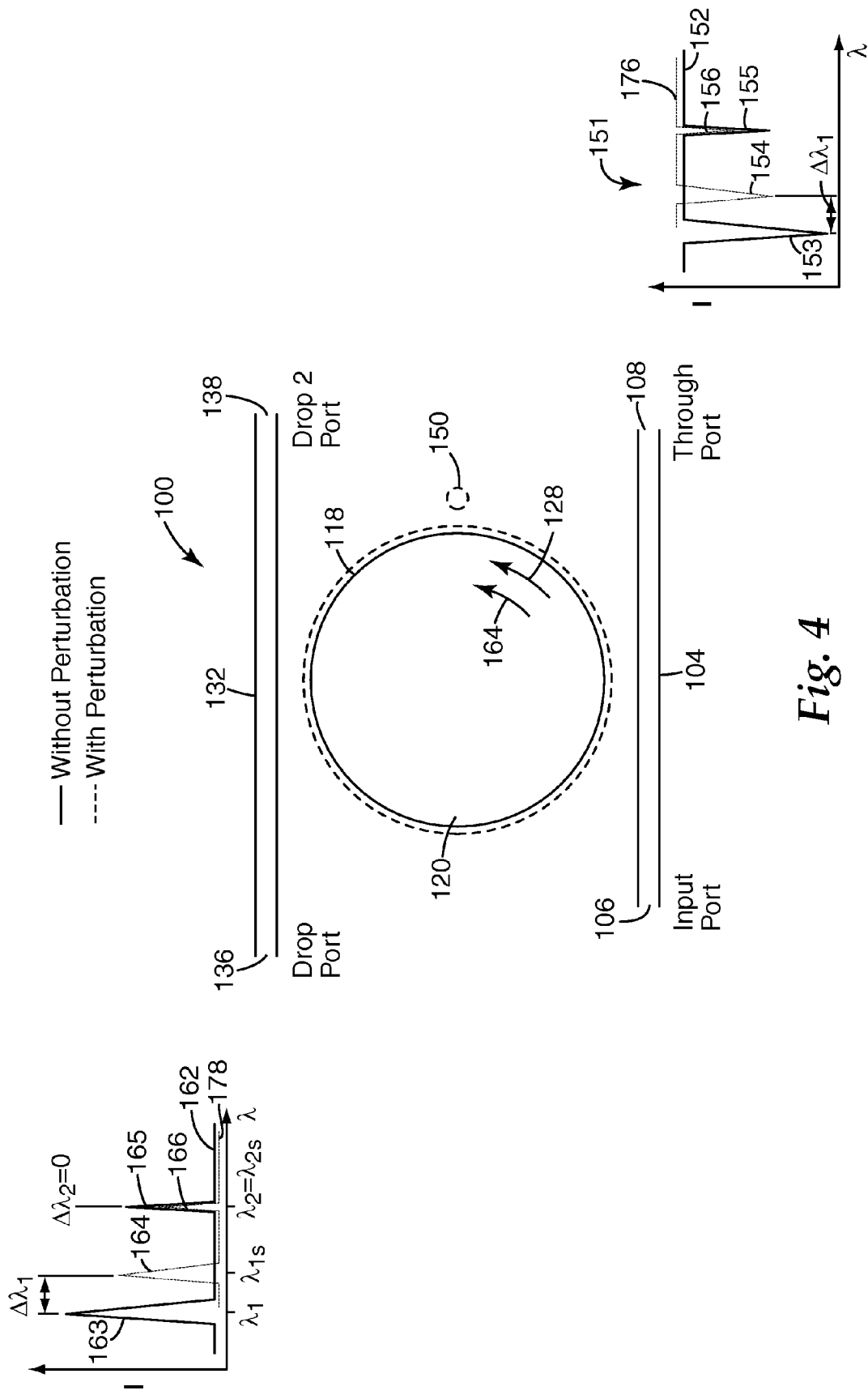
FIG. 4 illustrates the light output at the input and drop port detectors of FIG. 1 with and without a perturbation.

Another example of a perturbation is a change in the refractive index of a surface or a portion of a surface of the microresonator, such as is caused by a coating on the surface of the microresonator. Referring to FIG. 4, a representation of the light output is schematically illustrated for the optical system 100 including microresonator 118. Graphs illustrate a representation of the typical light output at the through port 108 and the drop port 136, with and without a perturbation. The solid line plots show the light output in the absence of a perturbation, while the dashed lines show the output in the presence of perturbation.

FIG. 4 illustrates two examples of a perturbation of the system 100. One example of a perturbation is a scattering center 150. Another example of a perturbation is a coating 159 which has the effect of changing the effective refractive index at the surface of the microresonator. Although both the scattering center 150 and the coating 159 are illustrated in FIG. 4, in one embodiment, only one of the scattering center 150 or the index-changing coating 159 is introduced to the system 100 to induce a frequency shift of the first and second optical modes.

For convenience, the process of sensing a change in optical coupling between a scattering center and a microresonator will first be described. The process is very similar when the perturbation is instead a change in the refractive index of the surface of the microresonator, as will be further discussed herein.

The presence of a scattering center 150 optically coupled to the microresonator causes a change in the output observed at the through port 108 and the drop port 136, as well as the output reflected to the input port 106 and drop 2 port 138. In one particular embodiment of the invention, a scattering center with a refractive index that is different than the cladding materials of the environment, which is water for most biosensing system, induces a large resonance line frequency shift for a first guided optical mode on the scale of nanometers. In some cases, there is a large difference between the cladding index and the scattering center index where each index can be a complex index of refraction. The frequency shift is conceptually illustrated in FIG. 4. At the through port 108, the solid line 152 of graph 151 illustrates the spectrum that is detected at through port detector 114 without a scattering center present, including an intensity drop 153 in the graph at a resonant wavelength of a first guided optical mode and an intensity drop 155 at a resonant wavelength characteristic of a second guided optical mode. Dashed line 176 illustrates the spectrum that is detected when a scattering center is brought into optical coupling with the microresonator. Low intensity points of the first guided optical mode, such as intensity drop 153, are shifted, such as to nearby intensity drop 154. In the exemplary graph 152, the shift is toward longer wavelengths or a red shift corresponding to, for example, the real part of the refractive index of the scattering center being greater than the index of the cladding materials. However, low intensity point 155 of the second optical mode is not shifted because the second optical mode has an evanescent field that is not significantly available for interaction with the scattering center 150.

A similar change is seen at the drop port 136, where dashed line 178 illustrates the spectrum with a scattering center, and solid line 162 illustrates the spectrum without a scattering center. The plot 162 without a scattering center includes an intensity peak 163 in the graph at a resonant wavelength of a first guided optical mode and an intensity peak 165 at a resonant wavelength characteristic of a second guided optical mode. Intensity peak 163 is shifted by $\Delta\lambda_1$ to intensity peak 164 after introduction of the scattering center. However, the wavelength of intensity peak 165 of the second guided optical mode is not significantly affected by the introduction of the scattering center, and becomes intensity peak 166 after the scattering center is introduced, which is present at essentially the same wavelength. As a result, the wavelength shift $\Delta\lambda_2$, and corresponding frequency shift, experienced by the second mode is zero.

The first and second modes of the microresonator 118 have different evanescent fields and thus different coupling to a scattering center or other perturbation. As a result, the magnitude of the induced shift depends on the specific resonant mode.

Figure 8:
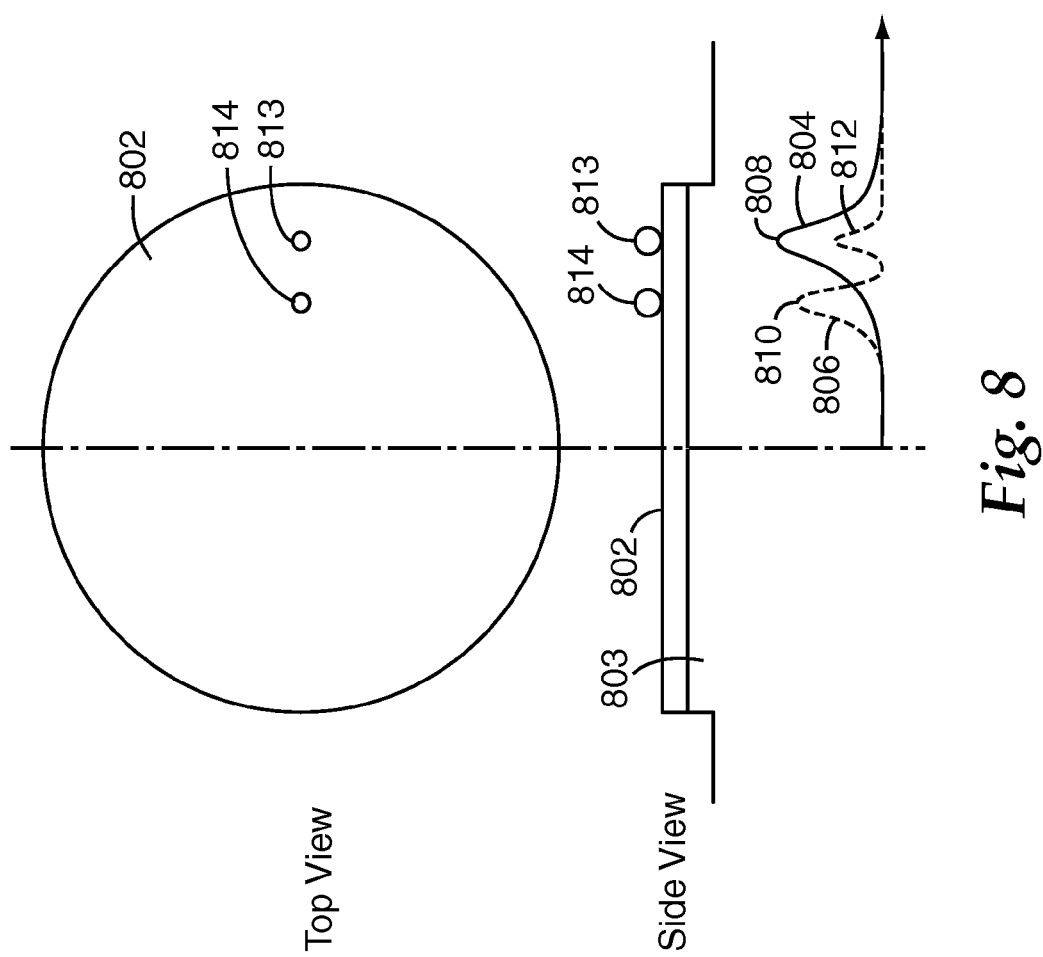
FIG. 8 is a schematic diagram showing a top and side view of a disk microresonator, along with a depiction of two radial modes of the microresonator.

For the example illustrated in FIG. 4, the scattering center 150 has a very small or no effect on the second optical mode 164. An example will now be discussed with reference to FIG. 5 where the second optical mode 164 experiences a measurable shift after a scattering center is coupled to the microresonator. This may occur where the characteristics of the microresonator are such that the second optical mode has an evanescent field that overlaps with the surface of the microresonator, such as depicted in FIG. 8, where second radial mode 806 has an evanescent field that overlaps with a nanoparticle at first position 813. Alternatively, the second optical mode may have experienced a measurable shift for reasons other than a change in coupling strength of the scattering center to the microresonator. For example, a temperature change of the system may change the refractive index of the cladding of the system, and this may result in a wavelength shift of the second optical mode.

Figure 5:
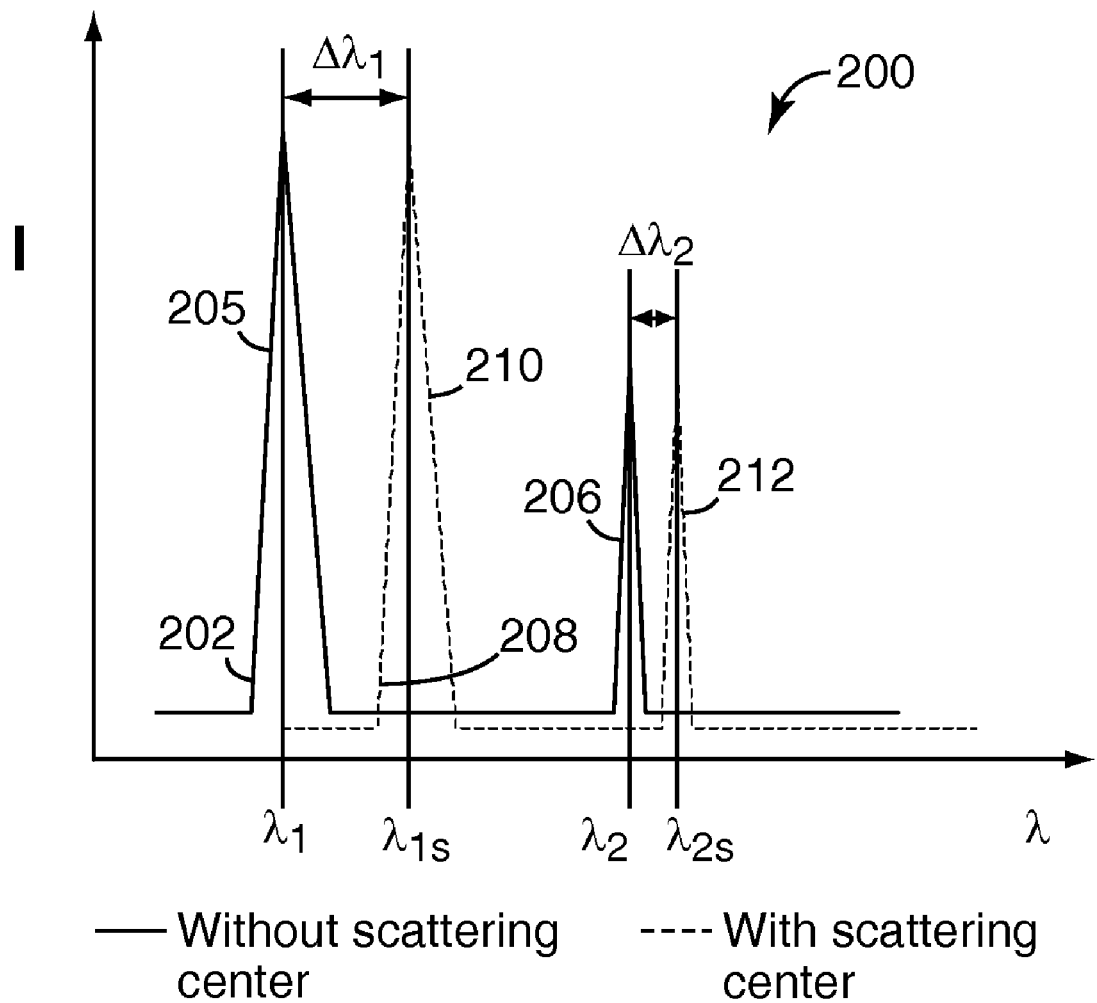
FIG. 5 illustrates the light output at a detector for one embodiment of FIG. 1, with and without a scattering center.

FIG. 5 illustrates light output at a drop port of one embodiment of a microresonator in graph 200. Solid line plot 202 illustrates the light output without a scattering center, and includes an intensity peak 205 at a first wavelength $v_1$ characteristic of a first optical mode and an intensity peak 206 at a second wavelength $v_2$ characteristic of a second optical mode. Dashed line plot 208 illustrates the light output at the drop port where a scattering center is in optical communication with the microresonator. The dashed line plot 208 includes an intensity peak 210 at a first wavelength $v_{1S}$ characteristic of a first optical mode and an intensity peak 212 at a second wavelength $v_{2S}$ characteristic of a second optical mode.

The wavelength shift of the first optical mode is:

$$\Delta\lambda_1 = \lambda_1 - \lambda_{1S}$$

The wavelength shift of the second optical mode is:

$$\Delta\lambda_2 = \lambda_2 - \lambda_{2S}$$

It is possible to determine the effect of the scattering center on the first optical mode, independent of other optical characteristic changes that may have occurred since the change in coupling strength of the scattering center, by subtracting the shift experienced by the second optical mode from the shift experienced by the first optical mode. The difference between the first frequency shift experienced by the first optical mode and the second frequency shift experienced by the second optical mode is:

$$\Delta\lambda_{SHIFT} = \Delta\lambda_1 - \Delta\lambda_2$$

The output at the through port detector 114 will also show a shift in the wavelength spectrum for the first and second optical modes, but the frequencies at the appropriate intensity minima of the spectrums will be used to calculate the difference between the first frequency shift and the second frequency shift.

In another method for using the output of a central detector 137, input detector 102 and/or drop 2 detector 144, backscattering is induced in the microresonator before the introduction of a perturbation. Without backscattering before the introduction of a perturbation, the output data from detectors at the input and drop 2 ports is not used in a self-referencing method because, as discussed above, there is no signal at these locations until a scattering center interacts with the resonator. As a result, there is no "before" signal to compare with the "after" signal to measure a shift. This is also the case with output at a center detector, because there is little signal at a microresonator center until a scattering center is coupled to the microresonator.

However, if a backscattered signal is generated before interaction with a perturbation, a signal will be detectable at the drop 2 port, input port and a center detector before the interaction with the perturbation begins. A backscattered signal can be generated in a number of ways, including introducing a permanent scattering center to the microresonator, to provide "before" signals to compare with the signal after the perturbation interaction begins. Examples of a permanent scattering center include a notch within the microresonator core of a different index of refraction than a remainder of the core, adequate surface roughness at the surface of the microresonator, or the angled sides of a polygonal microresonator. Also, there are many examples of scattering centers described herein that can be brought into and out of optical communication with the microresonator during a sensing process, such as nanoparticles, areas of variable refractive index, and others. These other types of scattering centers can be used with this method instead of a notch to create backscattering.

Figure 6:
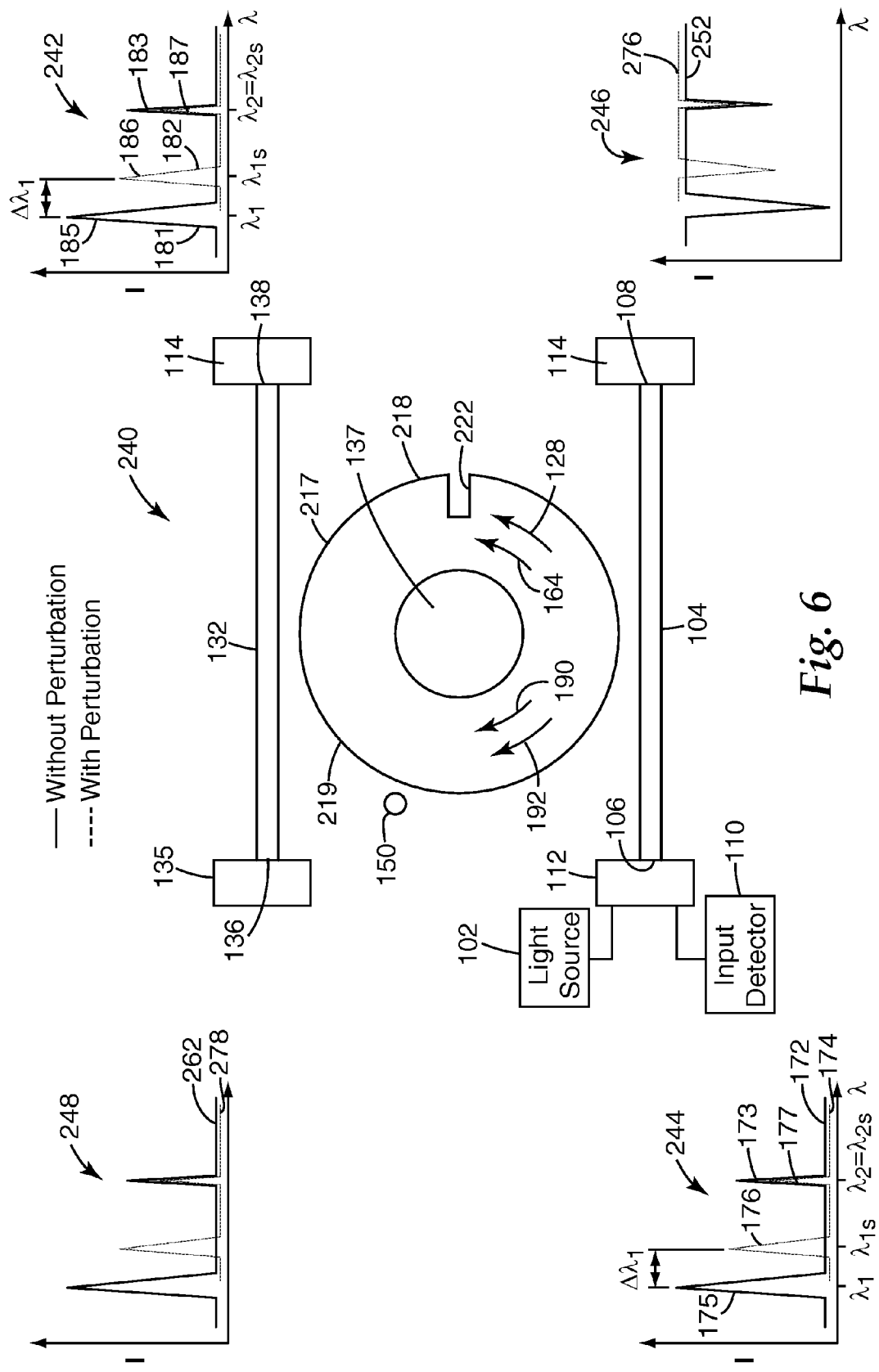
FIG. 6 is a schematic top-view of an alternative optical system including a microresonator having a scattering notch.

FIG. 6 illustrates this method in conjunction with an optical system 240 that is in many ways similar to the optical system 100 of FIGS. 1-4. Optical system 240 includes two bus waveguides 104 and 132, having an input port 106, through port 108, drop port 136 and drop 2 port 138. Optical system 240 also includes an input detector 102, a drop 2 detector 144 and a central detector 137. The disk microresonator 218 also includes a notch 222 having a different refractive index that the remainder of the core 217 of the microresonator 218. The notch 222 creates scattering of the optical modes of the microresonator, and as a result, significant peaks are observed at the central detector 137, the input detector 102 and the drop 2 detector 144. Light introduced by the light source 110 at the input port 106 excites first resonant optical guided mode 128 and second resonant optical guided mode 164. The notch 222 scatters the first and second guided optical modes 128 and 164 to third and fourth resonant optical modes 190 and 192, which are detected at the drop 2 and input ports, as discussed in more detail below. In addition, according to this method, a perturbation, such as a scattering center 150, causes a frequency shift in first and second modes 128 and 164. The frequency-shifted first and second modes are also scattered by the perturbation, and then the backscattered frequency-shifted first and second modes are detected as fifth and sixth optical modes at the drop two and input ports.

The third, fourth, fifth and sixth guided optical modes are detectable at the drop 2 and input ports. So, it is possible to compare a first frequency difference between third and fifth guided optical modes with a second frequency difference between the fourth and sixth guided optical modes. As discussed above with respect to the through port and drop port methods, this comparison illustrates any frequency shifting effect experienced by the system other than the introduction of the perturbation. As a result the effect of the perturbation can be isolated. FIG. 6 includes plots 242, 244, 246 and 248 that show a representation of the output at different ports of the system 240. If the optical coupling between a scattering center 150 or other perturbation and a microresonator is altered, then a shift of peaks can be observed at these three detector locations.

At the input port 106, the solid line 172 of graph 244 illustrates the spectrum that is detected at input port detector 102 without a perturbation present such as scattering center 150, but with some type of scattering center present, such as notch 222. Plot 172 includes an intensity peak 175 in the graph at a resonant wavelength of a third guided optical mode and an intensity peak 173 at a resonant wavelength characteristic of a fourth guided optical mode. Dashed line 174 illustrates the spectrum at the input port that is detected after a scattering center is brought into optical coupling with the microresonator. Intensity peaks of the third guided optical mode, such as intensity peak 174, are shifted, such as to nearby intensity peak 176. In the exemplary graph 244, the shift is toward longer wavelengths or a red shift corresponding to, for example, the real part of the refractive index of the scattering center being greater than the index of the cladding materials. However, intensity peak 173 of the fourth optical mode is not shifted because the second optical mode has an evanescent field that is not significantly available for interaction with the scattering center 150. As a result, the fourth optical mode that is backscattered from the second optical mode also does not display an impact of a change in coupling of the scattering center 150. The intensity peak 177 is therefore at about the same wavelength as intensity peak 173.

A similar change is seen at the drop 2 port 138, where solid line 181 illustrates the spectrum before a perturbation, such as a scattering center 150, is introduced, and dashed line 182 illustrates the spectrum after a scattering center is introduced. The output is very similar to that of the input port 106, where a third mode 185 is shifted by $\Delta\lambda_1$ to a peak 186, and a fourth mode 183 experiences little or no shift to peak 187, so that the wavelength shift $\Delta\lambda_2$, and corresponding frequency shift, experienced by the second mode is zero.

The detection of scattered and frequency shifted modes is very similar at a center detector 137 location as described above for the drop 2 and input ports. The detected spectrum will be very similar to plots 242 and 244. One difference is that the scattered modes detected at the center detector 137 are not resonant modes. The center detector will detect the third and fourth optical modes that are scattered from the first and second optical modes. The center detector will also detect fifth and sixth optical modes that are scattered from the first and second frequency-shifted optical modes. The frequency shift from the third to fifth optical modes and the fourth to fifth optical modes will then be determined.

As mentioned previously, the notch 222 is not the only way to provide backscattering so that the drop 2 port, input port, and center detector ports can be used in a self-referencing method. A sufficient surface roughness of the surface 219 of the microresonator can also provide backscattered modes. In one embodiment, the surface 219 has a surface root mean square (Rq) roughness of about 50 nanometers or greater. In another embodiment, the surface roughness (Rq) is about 75 nanometers or greater.

Figure 7:
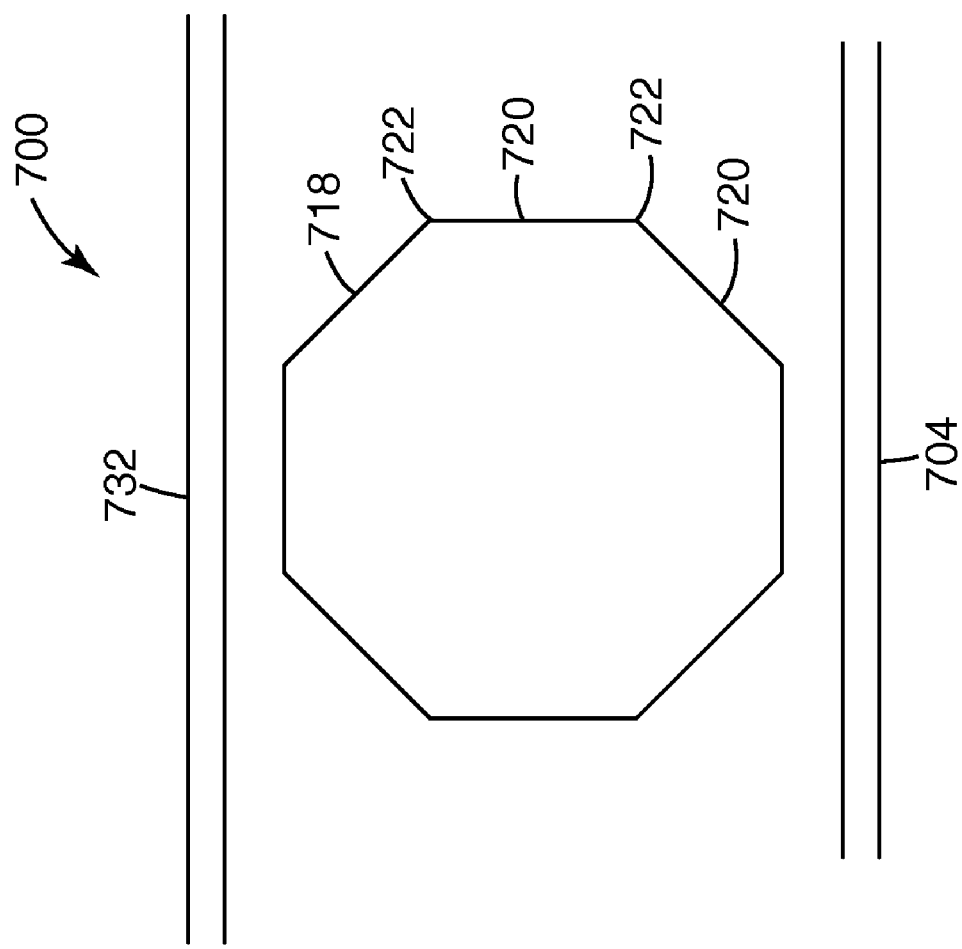
FIG. 7 is a schematic top-view of an alternative optical system including a polygonal microresonator.

In other embodiments, a polygonal resonator provides backscattering sufficient to generate signals at the drop 2 and input ports and the center detector. FIG. 7 illustrates an optical system 700 having an octagonal microresonator 718, a first bus waveguide 704 and a second bus waveguide 732. The optical system 700 includes other components, similar to those illustrated in FIGS. 1-4, in various embodiments, but those are not illustrated in FIG. 7 for simplicity. The angled sides 720 and junctures 722 between the angled sides provide surfaces for backscattering so that the method described with relation to FIG. 6 can be performed without a notch 222.

In addition to octagonal microresonators, other types of polygonal resonators may be used as microresonators that provides backscattered modes. For example, hexagonal and pentagon microresonators may be used.

The plots 246 and 248 at the through port 108 and drop port 136, respectively, also show a frequency shift between the solid plots before a perturbation 252 and 262 and the dashed line plots after a perturbation 276 and 278. As discussed above with relation to FIG. 4, a shift occurs at these ports even in the absence of an initial scattering center, so it is not necessary to have an initial scattering center such as notch 222 to take advantage of the frequency shift at the through port 108 and drop port 136. The output at these two ports is similar in spectrum to what occurred without an initial scattering center as shown in FIG. 4, but will have a lower intensity because light is being scattered to additional ports compared to the situation presented in FIG. 4.

Different scattering centers used to provide backscattering will scatter to varying degrees. Note that in the case of fairly strong scattering from a scattering center, such as the notch 222, splitting of some of the wavelength peaks can occur. This is the result of the standing-wave nature of the resonant modes with strong scattering, and the fact that two different types of standing-wave modes are possible: one with an electric field node centered at the notch, and one with an electric field antinode centered at the notch. These two modes have slightly different effective indices, and thus have slightly different wavelength. The splitting is often not observed experimentally, because either the resonator linewidth (related to Q), or the detection system frequency resolution, are inadequate to resolve the small splitting (see Little et al, "Second order filtering and sensing with partially coupled traveling waves in a single resonator", Optics Letters Vol 23, pg 1570 (1998)).

In many of the cases of self-referencing microresonator system embodiments discussed herein, the differential interaction between a perturbation and the resonator modes is based on the inherent difference in the resonant mode shape, with no effort made to control the region of the resonator where the perturbation can interact with the mode in the core of the resonator. In some embodiments, it may be advantageous to control the region of the resonator where the perturbation can interact with the optical modes; this can be used to enhance the difference in the effect produced by the perturbation on the modes.

FIG. 8 depicts a top view and a side view of a core 802 of a disk microresonator positioned on a lower cladding 803, in which two whispering-gallery resonant modes are excited, corresponding to two radial solutions of the wave equation for the disk cavity. The curves 804 and 806 depicting the modes correspond to the square of the electric field amplitude in the modes. The radial modes are Bessel functions of order m satisfying the wave equation and boundary conditions. The first mode 804 has a single lobe 808 (maximum) within the disk, and the second mode 806 has two lobes 810 and 812 within the disk. When a perturbation interacts with the modal evanescent field at the top of the disk, the strength of the coupling is dependent on the strength of the modal field at the coupling location. Thus a perturbation at a first location 813 will affect both the first and second radial modes, but the first mode more strongly than the second. A perturbation at a second location 814 will affect primarily the second mode.

Since each mode corresponds to a different free-space wavelength, the location of the perturbation on the resonator surface controls how the spectrum near each mode wavelength is affected. By detecting the effect at different resonant wavelengths, the radial location of the perturbation to the microresonator cavity can be inferred.

In some cases it may be desirable to minimize the effect of the perturbation on one mode, in order to use that mode as a reference wavelength. This can be done in variety of ways, some of which are discussed below.

Figure 9:
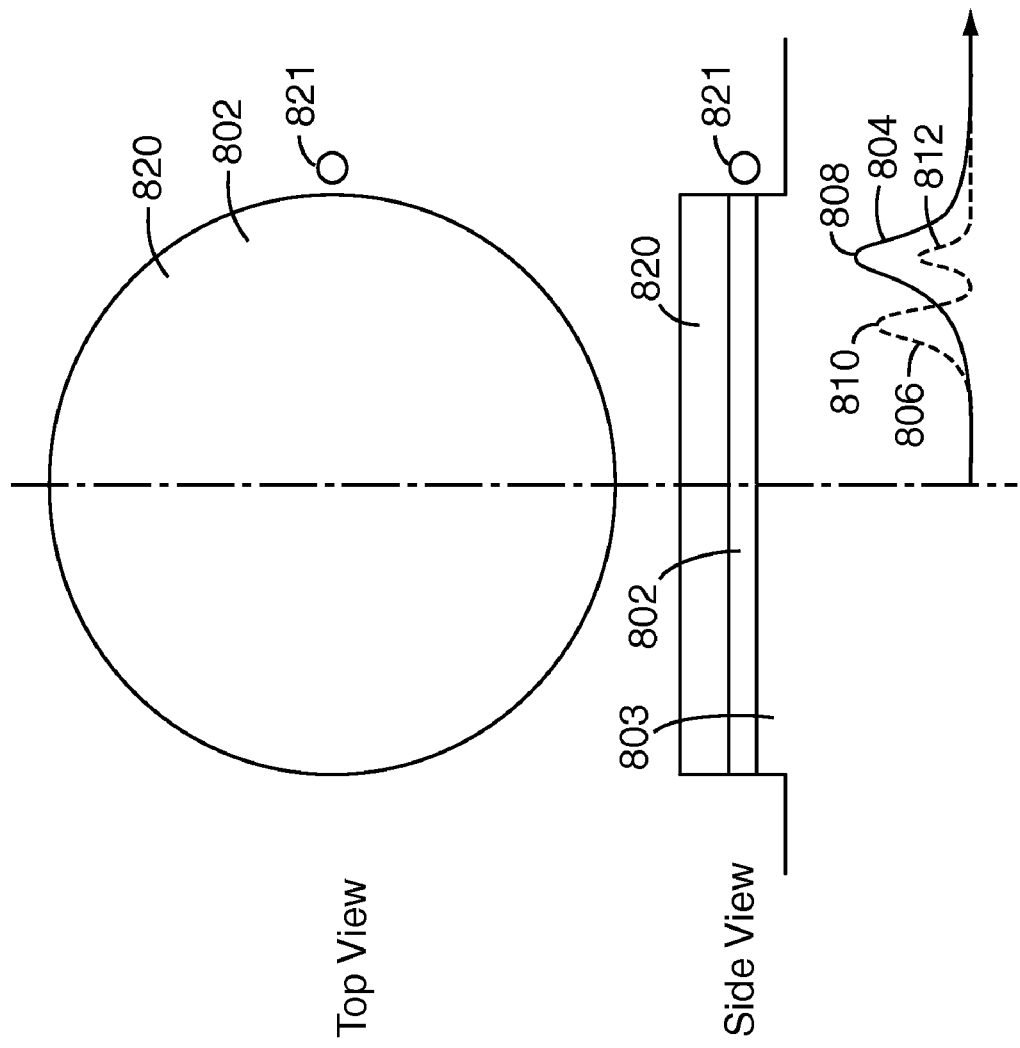
FIG. 9 is a schematic diagram showing a top and side view of a disk microresonator having a patterned cladding, along with a depiction of two radial modes of the microresonator.

FIG. 9 depicts a core 802 of a disk microresonator similar to that shown in FIG. 8, except that in FIG. 9 the disk is provided with an upper cladding 820 which has a low index of refraction compared to the core. This prevents the perturbation, such as scattering center 821, from affecting the resonator field except at the cylindrical side surface 822 of the resonator disk. In disk resonators, the two-lobed second mode 806 typically has a much lower electric field intensity at the periphery of the disk than the single-lobed first mode 804, thus the perturbation has a much stronger effect on the first mode. If the perturbation is provided by an analyte binding to the resonator, and the analyte is to be detected by a wavelength shift method, the wavelength corresponding to the second mode will shift very little when the analyte binds to the periphery, whereas the wavelength corresponding to the first mode will shift much more. Comparison of the first and second mode wavelengths thus provides a self-referencing effect for detection of the analyte.

The area covered by the cladding 820 defines an unavailable portion of the surface of the microresonator that is not available for interaction with a perturbation. In certain embodiments, the unavailable portion is distinct from coupling regions, such as coupling regions 145 and 147 illustrated in FIG. 1, where the microresonator is optically coupled to the one or more bus waveguides that are a part of the system.

Figure 10:
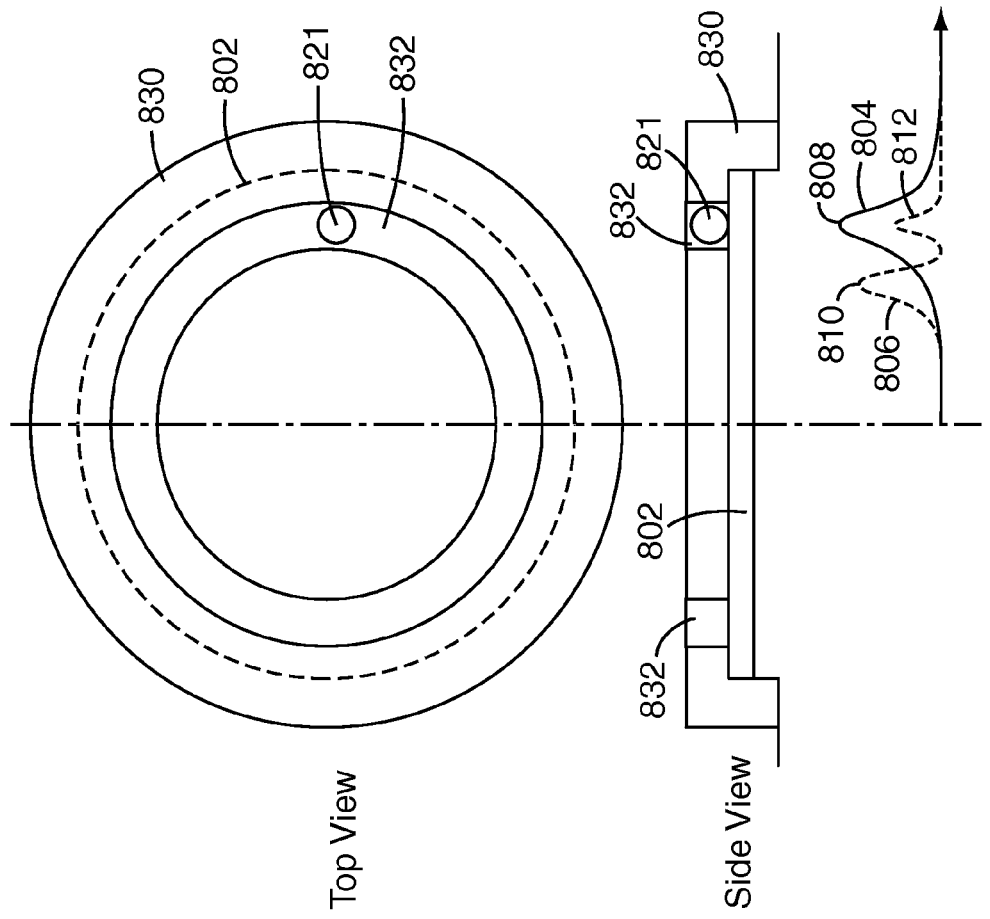
FIG. 10 is a schematic diagram showing a top and side view of a disk microresonator having an alternative patterned cladding layer, along with a depiction of two radial modes of the microresonator.

FIG. 10 depicts another disk resonator having a core 802, again with the location of the pertubation controlled by cladding 830. In FIG. 10, upper cladding 830 is applied over the entire top of the core, and then patterned to have an open area 832 in an annular shape that only allows the resonator to be perturbed at a location corresponding to the peak intensity of the second mode (two-lobed) mode. In this way the effect of the pertubation on the second mode can be made stronger than the effect of the perturbation on the first mode.

Figure 11:
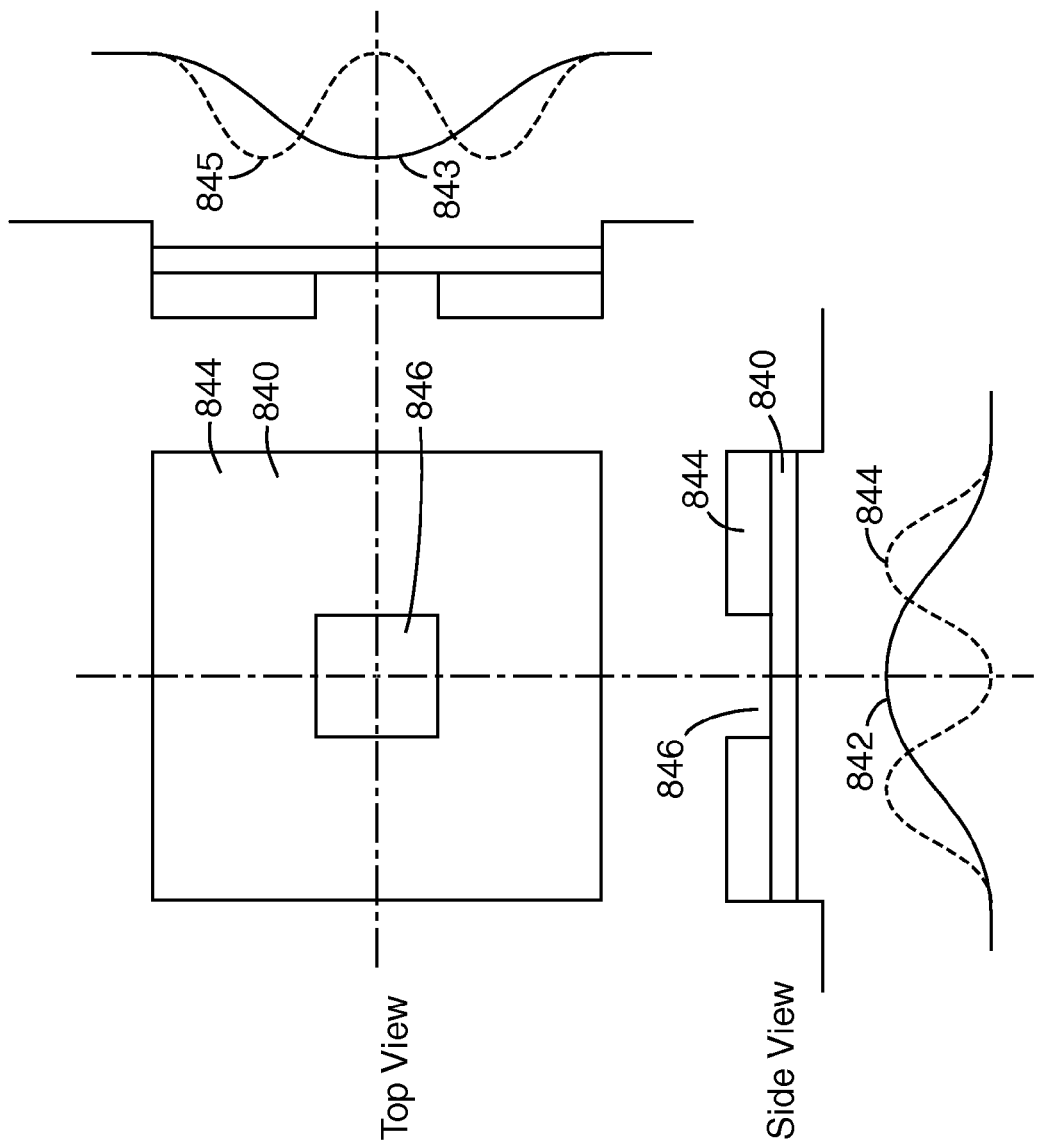
FIG. 11 is a schematic diagram showing a top and side view of a rectangular microresonator having a patterned cladding layer, along with a depiction of four modes of the microresonator.

FIG. 11 is a schematic depiction of an exemplary different geometry for the microresonator. In this case, the resonator is a rectangular resonator 840, taken here for simplicity to be a square. This resonator can support a large number of standing wave resonant modes. For simplicity of depiction, only the spatial dependence of the square of the electric field amplitude for the longest-wavelength resonances in the x direction, 842 and 844, and 843 and 845 in the y direction of the cavity are shown. In this case low-index upper cladding 844 has been added to the resonator so that the perturbation can only interact with the resonator field in a central open region 846 of the resonator. This maximizes the effect of the perturbation on the single-lobed horizontal mode 842 and the single-lobed vertical mode 843, and minimizes the effect of the perturbation on the two-lobed modes 844 and 845. Therefore, in a frequency shift detection approach, the wavelength corresponding to the first mode which is single-lobed in the horizontal and vertical direction will shift the most when an analyte binds in the sensing region, and the wavelength corresponding to the second mode which is two-lobed in both the horizontal and vertical directions will shift the least. Thus the second mode provides a reference signal for self-referencing.

The above embodiments are just examples of patterned cladding configurations, and do not in any way limit the concept of using cladding on a microresonator to enhance or suppress the effect of an external perturbation on one or more spatially localized modes of a microresonator.

The method for using the systems of the invention has been described mostly in the context of using a scattering center as a perturbation. However, another type of perturbation is a change in the index of refraction of the surface of the microresonator or a portion of the surface of the microresonator. As in the case of coupling to a scattering particle, patterning of the surface cladding can enhance the difference between the effects on different resonator modes.

For the microresonator system 700 of FIGS. 9-10, for example, the annular-shaped available portion provides an opportunity for coating the surface of the microresonator to change the index of refraction in the available portion. Such a coating causes a shift in the first optical mode of the microresonator, while causing a negligible shift or no shift in the second optical mode of the microresonator, similar to the different shifts discussed above with respect to FIGS. 4 and 5. As described above, those shifts are used to determine whether a perturbation has coupled with the microresonator.

An alternative method for controlling the interaction of an analyte with the spatially-localized modes of a microresonator is to coat the surface of the microresonator with a patterned layer of a chemical species that selectively binds to the analyte. This approach is shown schematically in FIG. 12, where a chemical binding functionalization is applied in an annulus, designed to coincide with a field maximum of one of the radial modes of the resonator.

Figure 12:
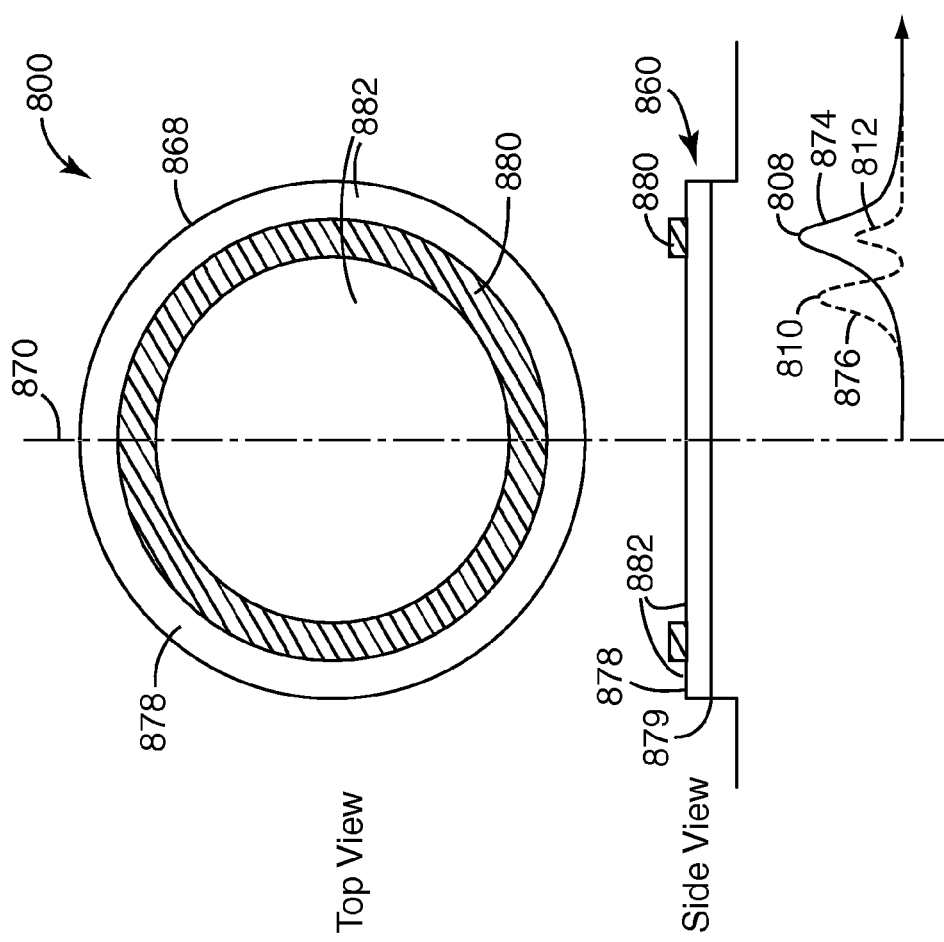
FIG. 12 is a schematic diagram showing a top and side view of a disk microresonator having a functionalization layer, along with a depiction of two radial modes of the microresonator.

FIG. 12 includes a top view and a side view of a disk microresonator 868, where the two views are both centered on an axis 870 representing a central axis of the system. In addition, FIG. 12 illustrates two whispering-gallery resonant modes that are excited in the microresonator 868, corresponding to two radial solutions of the wave equation for the disk cavity. The curves 874 and 876 depicting the modes correspond to the square of the electric field amplitude in the modes, and are illustrated to show how the intensity of these modes vary with distance from the central axis 870. The radial modes are Bessel functions of order m satisfying the wave equation and boundary conditions. The first mode 874 has a single lobe (maximum) within the disk, and the second mode 876 has two lobes within the disk, like the situation discussed above with relation to FIGS. 8-10.

The microresonator 868 has a top planar surface 878 and a cylindrical side surface 879. The top surface 878 includes a chemical binding functionalization coating 880 in an annular pattern that will chemically bond to the analyte. The uncoated area 882 will not chemically bond to the analyte. The functionalization coating 880 binds to the analyte in the annular shape, so that index of refraction change caused by the binding of the analyte to the functionalization area will perturbed the microresonator at a location corresponding to the peak intensity of the second mode (two-lobed) mode. In this way the effect of the binding of the analyte on the second mode can be made stronger than the effect of the perturbation on the first mode. In one embodiment, analyte that contacts functionalized annular portion 880 is more likely than not to bind to the microresonator surface. In various embodiments, the analyte is highly likely, such as 90% or more, to bind to the microresonator surface at the functionalized annular portion 880.

In an alternative embodiment to FIG. 12, a coating that prevents chemical bonding is present on area 882, including the cylindrical side surface 879 of the microresonator. As a result, analyte that contacts the microresonator at area 882 is unlikely to adhere to the microresonator surface.

Embodiments of the present invention have been described that include a disk microresonator that is capable of supporting at least two guided resonant optical modes. Alternative embodiments of the system include other shapes of microresonators, as long as they are capable of supporting at least two guided resonant optical modes and their spatial geometry permits a perturbation at a surface of the microresonator to have different effects on first and second optical modes of the microresonator. Other examples of microresonator configurations that can be used with the present invention include a multi-mode ring resonator and a multi-mode racetrack resonator, and polygonal resonators.

Figure 13:
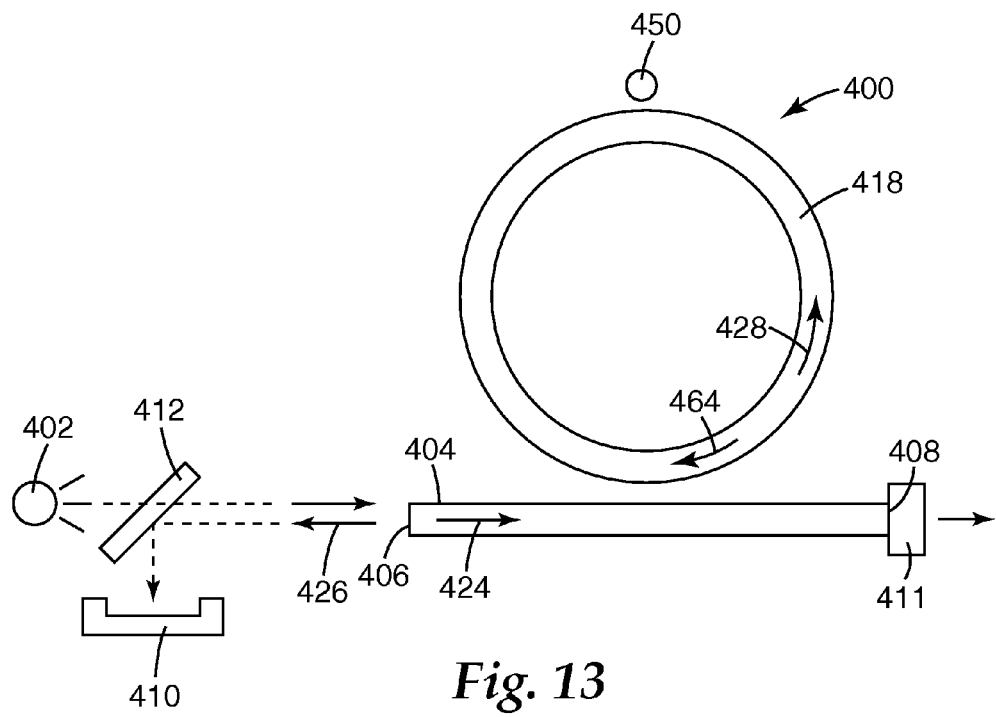
FIG. 13 is a schematic top-view of an optical system with a single-bus ring resonator.

FIG. 13 is a schematic illustration of a single bus ring resonator embodiment 400, where a light source 402 is in optical communication with the single waveguide 404 at an input port 406. An input port detector 410 is positioned at the input port 406, which can be utilized in the self-referencing method if a scattering center is present to generate backscattered modes before a perturbation is introduced. An optical component 412, such as an optical splitter or optical circulator, is in optical communication with the input port 406, the light source 402, and the input port detector 410. A through port detector 411 is in optical communication with the through port 408.

A ring microresonator 418 is in optical communication with the waveguide 404. Light 424 from the light source 402 is launched into the first bus waveguide 404 and propagates towards the through port 408. The microresonator 418 evanescently couples some of the light 424 out of the first bus waveguide 404, the out-coupled light propagates within the microresonator 418 at two or more of the resonant frequencies of the microresonator 418, such as first resonant optical mode 428 and second resonant optical mode 464.

During a sensing event according to one embodiment of the present invention, the strength of optical coupling between a microresonator 418 and a scattering center 450 or another perturbation is altered. When a scattering center 450 or other perturbation is in optical communication with the microresonator, the first guided optical mode 428 experiences a wavelength shift. The second guided optical mode 464 experiences a different wavelength shift, which may be no wavelength shift.

An alternate embodiment, includes only one of the input detector 410 and the through port detector 411. In another alternative embodiment, the ring resonator 418 is replaced with a disk resonator.

Figure 14:
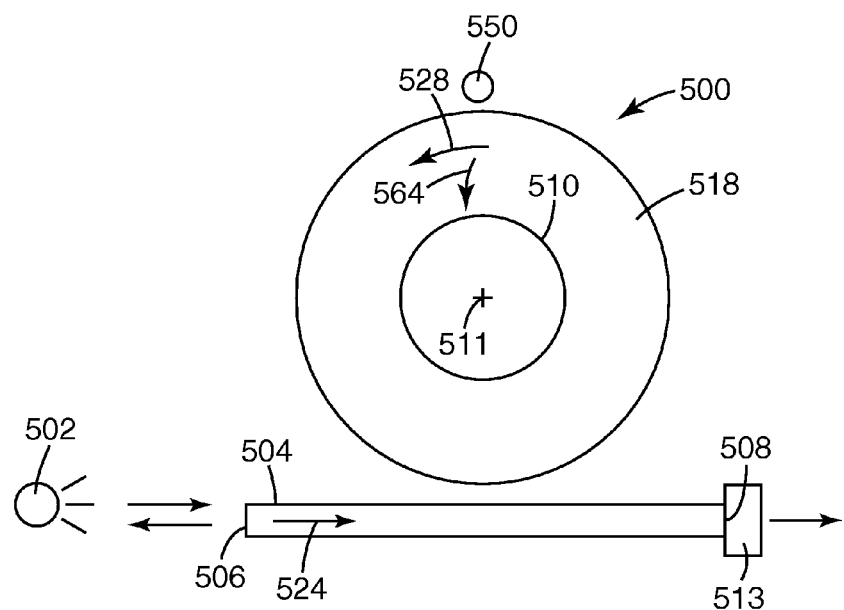
FIG. 14 is a schematic top-view of an optical system with a single-bus disk resonator with a center photodetector.

FIG. 14 is a schematic illustration of a single bus disk resonator embodiment 500, including a light source 502 in optical communication with the single waveguide 504 at an input port 506, to provide light 524 to the waveguide 504. A center light detector 510 is positioned at a center 511 of a disk resonator 518. Another detector 513 is positioned at the through port 508. In alternative embodiments, only one of the detectors is present.

A scattering center 550 is brought into or removed from optical communication with microresonator 518. For the illustrated embodiment, the step of detecting a wavelength shift for the first resonant optical mode 528 and a second guided optical mode 564 includes detecting the wavelengths transmitted to the through port 508, and detected by detector 513. Output detected by the center detector 510 at the center location 511 can be utilized in the self-referencing method if a separate scattering center is present to generate backscattered modes before a perturbation, such as scattering center 550, is introduced.

Figure 15:
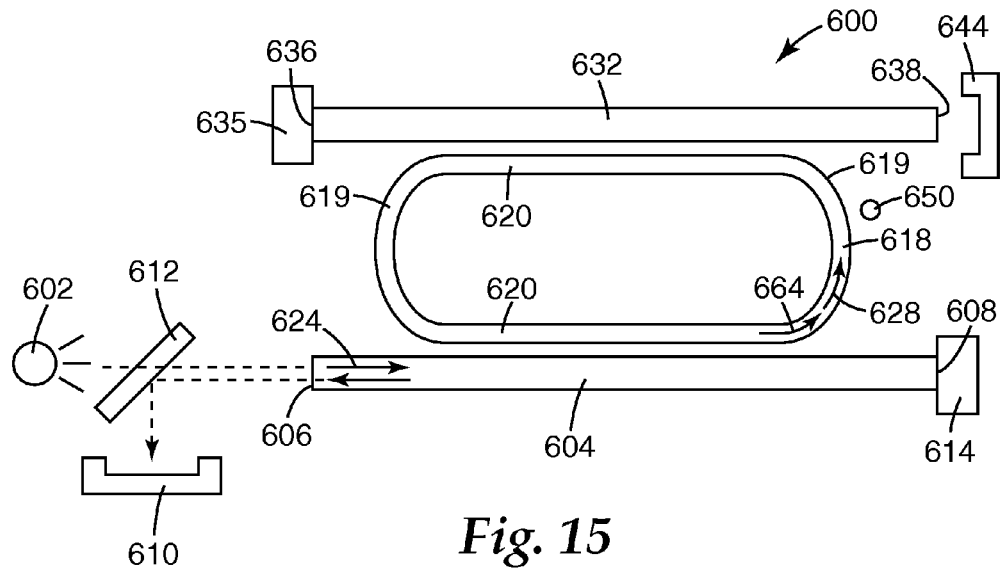
FIG. 15 is a schematic top-view of an optical system with a double-bus racetrack ring resonator.

FIG. 15 is a schematic view of a double bus waveguide racetrack microresonator embodiment 600, where a light source 602 is in optical communication with a first waveguide 604 at an input port 606. An input port detector 610 is positioned at the input port 606. An optical component 612, such as an optical splitter or optical circulator, is in optical communication with the input port 606, the light source 602, and the input port detector 610. A through port detector 614 is present at a through port 608 at the other end of the first waveguide 604.

Light 624 from the light source 602 is launched into the first bus waveguide 604 and propagates towards the through port 608. A multi-transverse mode racetrack microresonator 618 includes two curved portions 619 and two linear portions 620. The microresonator 618 evanescently couples some of the light 624 out of the first bus waveguide 604, the out-coupled light propagates within the microresonator 618 at two or more of the resonant frequencies of the microresonator 618, such as first resonant optical mode 628 and second resonant optical mode 664.

A second bus waveguide 632 is positioned in optical communication with the microresonator 618. A drop port 636 and drop port detector 635 are located at one end of the second bus waveguide 632, while a drop 2 port 638 is located at another end of the second bus waveguide 632. The drop port 636 is primarily capable of optically coupling to the first guided optical mode 628. The drop 2 port 638 is capable of very weak coupling or is not capable of coupling to the first guided optical mode. A drop 2 port detector 644 is located at the drop 2 port 638.

The effect of altering the coupling strength of a scattering center 650 on first and second optical modes can be observed at the through port 608 and drop port 636, as discussed above with respect to other microresonator systems. Output detected by the input port detector 610 or drop 2 port detector 644 can be utilized in the self-referencing method if a separate scattering center is present to generate backscattered modes before and in addition to the introduction of a perturbation such as scattering center 650. Accordingly, various embodiments include detectors in optical communication with one or more of these four detector locations.

Additional embodiments of microresonator waveguide systems that can be configured to support both a first resonant guided optical mode and a second guided optical mode and can be utilized with the self-referencing methods and devices of the present invention are illustrated and described in commonly-owned U.S. patent application Ser. No. 11/565,935, titled "Optical Microresonator", filed on Dec. 1, 2006, and in commonly-owned U.S. patent application Ser. No. 11/616,338, titled "Optical Microresonator", filed on Dec. 27, 2006, the entirety of which were previously incorporated herein by reference.

As discussed previously, a perturbation is a change of an optical characteristic of the microresonator. For example, a change in the refractive index of a surface or a portion of the microresonator, such as is caused by a coating on the surface of the microresonator or an optical coupling of the microresonator to a scattering center.

A scattering center is an element that, when optically coupled to a microresonator, is able to perturb the wave function of the resonant modes within the microresonator to cause a transfer of energy from modes that are excited by input in the absence of the scattering center (such as at least first resonant optical mode 128 in FIG. 1) to modes that are not excited in the absence of the scattering center. In an embodiment, the scattering center increases the transfer of energy from a first mode to another mode, though some transfer of energy from the first mode to other mode may occur even in the absence of the scattering center.

In addition, the interaction of the scattering center with the modal field of the microresonator changes the effective refractive index of the mode, assuming that the center has a different refractive index from the cladding. This shifts the resonant wavelength of the mode.

Examples of scattering centers that may be used with the present invention sensing methods include nanoparticles. As used herein, the term "nanoparticles" refers to particles having a maximum dimension on the order of 1000 nanometers or less. In certain embodiments, the scattering center is at least 20 nanometers, at most 100 nanometers, or both. In other embodiments, the scattering center is at least 10 nanometers, at most 150 nanometers, or both.

In one embodiment of the invention, the scattering center has a high index difference compared to the medium that will surround the scattering center during a sensing event, which is typically water. In an embodiment of the invention, the scattering center has a high absorption value. For example, the imaginary part of the complex refractive index of the scattering center material is at least 8.

In some cases, such as in the case of some metals such as gold, the real part of the index of refraction of the scattering center is less than 1. In some other cases, such as in the case of silicon, the real part of the index of refraction of the scattering center is greater than 2.5.

Examples of scattering centers that are appropriate for use with the invention include silicon nanoparticles and metal nanoparticles, including gold and aluminum nanoparticles. In some cases, a scattering center may be a semiconductor such as Si, GaAs, InP, CdSe, or CdS. For example, a scattering center can be a silicon particle having a diameter of 80 nanometers and an index of refraction (the real part) of 3.5 for a wavelength of interest. Another example of a scattering center is a gold particle having a diameter of 80 nanometers and an index of refraction of 0.54+9.58i for wavelengths near 1550 nm. Another example of a scattering center is an aluminum particle having a diameter of 80 nanometers and an index of refraction of 1.44+16.0i for wavelengths near 1550 nm.

In some embodiments, the scattering center is a dielectric particle. In some embodiments, the scattering center has a different birefringence, magnetic susceptibility, or electric susceptibility, than the upper cladding that surrounds it. The scattering center is a ferromagnetic or paramagnetic particle in various embodiments. The scattering center is a non-fluorescent particle in many embodiments. Further, the scattering center is not a semiconductor in some embodiments.

In some embodiments, the scattering center is a metamaterial.

One example of perturbations that change the refractive index of a portion of a surface of a microresonator is a coating on the surface of the microresonator such as antibody that can bind other proteins to the resonator surface, or a coating with a porous polymer that can absorb solvent vapors and thereby change refractive index.

Now referring to the example of FIG. 1 to illustrate an issue that relates to all the examples, a change in the strength of optical coupling between scattering center 150 and microresonator 118 can induce a change in optical scattering between first and second guided optical modes 128 and 164, respectively. The change in the strength of optical coupling can be achieved by various means. For example, a change in the spacing "d" between scattering center 150 and microresonator 118 can change the strength of optical coupling between the scattering center and the microresonator. In another example, a change in the index of refraction, $n_s$, of the scattering center can change the strength of optical coupling between the scattering center and the microresonator. In one embodiment, the scattering center is a region of variable refractive index embedded in the core of the resonator. In such a case, the index of refraction can change when, for example, the region is exposed to and absorbs a material such as gas or liquid. In general, any mechanism that can cause a change in the strength of optical coupling between scattering center 150 and microresonator 118 can induce a change in optical scattering between modes 128 and 164.

There are several approaches to using the microresonator waveguide system as a sensor. The choice of approach is determined by a variety of considerations, including the chemistry of the analyte to be detected, the time available for detection, the sample preparation technology, etc. One example of using a scattering center in a detector system involves coating the resonator with an antibody for a specific antigen. An antibody is a protein used by the immune system to identify and neutralize foreign objects like bacteria and viruses. Each antibody recognizes a specific antigen as its unique target.

In one approach, the sample to be analyzed is prepared such that scattering center labels, such as nanoparticle labels, are selectively attached to the antigen molecules, by functionalizing the nanoparticles with a corresponding antibody before mixing them with the sample. The sample is then brought into contact with the surface of the microresonator. When the binding between the antibody-functionalized resonator and the nanoparticle-labeled antigen occurs at the surface of the resonator, the nanoparticle is brought into optical coupling range. As a result, the first optical mode experiences a wavelength shift at the drop port or through port, which is detected. Also, a signal would be detected at the a central detector, drop two port detector or input port detector where there previously was not a significant signal. The same or a similar approach is used to detect bacteria, viruses and spores, as well as protein and DNA.

Sensing by removal of a scattering center from the resonator is accomplished by first binding the scattering center to the resonator with an antigen-antibody system having weaker binding than the antigen-antibody reaction resulting when the analyte is introduced. Competition for binding to the resonator would result in separation of the scattering center from the vicinity of the resonator, and loss of optical coupling with the scattering center. A similar approach allows detection of any chemical species capable of selectively severing chemical bonds between the nanoparticle and resonator.

The light source 102 generates light 124 at a desired wavelength, or wavelength range. For example, where the microresonator is used in a sensor, the light source 102 generates light at a wavelength that interacts with the scattering center that is being introduced to or removed from optical communication with the microresonator. In existing sensing systems using microresonators, it is particularly important that the light source produces light that is efficiently coupled into the first bus waveguide 104. This leads to the frequent use of light sources such as lasers, such as a laser diode. Lasers, such as laser diodes, are appropriate light sources for use with embodiments of this invention. In addition, the approach of the present invention allows the use of a light source that generates a broader range of wavelengths than light sources in existing sensing systems. In an embodiment, the light source 102 includes a lamp, along with suitable optics for coupling light from the lamp into the first bus waveguide 104. In some applications, light source 102 can be a light emitting diode (LED) or a laser such as a laser diode. In an embodiment, the lamp is a broadband light source, emitting a number of or a range of frequencies rather than one specific wavelength or narrow range of wavelengths. In some applications, the light source can be a broadband light source emitting, for example, white light. In some cases, light source 102 can emit light having at least one wavelength in a range from about 400 nm to about 2000 nm. In some other cases, the range can be from about 700 nm to about 1600 nm. In some other cases, the range can be from about 900 nm to about 1400 nm. In some cases, light source 102 can emit light at 633 nm, 850 nm, 980 nm, 1310 nm, or 1550 nm.

The difference between the first and second wavelengths can be detected using optical heterodyne detection techniques, which analyze beat frequencies between two slightly different optical frequencies.

The first bus waveguide 104 may be any suitable type of waveguide and may be, for example, a channel waveguide formed in or on a substrate, such as a waveguide formed in or on a silicon substrate. The first bus waveguide 104 may also be an optical fiber.

The detector unit 110 includes a light detector, for example a photodiode or phototransistor, to detect light. The detector unit 110 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector. In some cases, a wavelength selective device may be employed at other ports such as the drop two port.

Microresonator 118 of FIG. 1 is shown to be a disk microresonator. Alternative embodiments of the system include other shapes of microresonators, as long as they are capable of supporting at least two guided resonant optical modes and their spatial geometry permits a perturbation at a surface of the microresonator to have different effects on first and second optical modes of the microresonator. For example, microresonator 118 can be a multi-mode ring resonator, a multi-mode racetrack resonator, or a polygonal resonator.

In the various exemplary embodiments discussed herein, any of these microresonator types could be substituted for another to create alternate embodiments. Since the fabrication process for ring and disk microresonators is compatible with standard microelectronic processes, these devices offer considerable potential for low cost manufacturing and robust systems.

In some cases, the microresonator has circular symmetry, meaning that the perimeter of a cross-section of the core of the microresonator can be expressed as a function of distance from a central point only. In some cases, such as in a disk-shaped microresonator, the center point can be the center of the microresonator. Exemplary microresonator shapes having circular symmetry include a sphere, a toroid, a disk, and a cylinder.

The microresonator 118 typically has a diameter in the range from 2 μm to a few millimeters, but is more often in the range 5 μm-500 μm. In some cases, the range is from about 5 μm to about 100 μm.

In some cases, the bus waveguides and the microresonators as well as the light sources and the detectors of this invention are integrated onto a common substrate. The integration may be a monolithic integration, in which case the different components are all fabricated onto the common substrate typically using the same material systems. Such an integration can be substrate specific, meaning that the integration may be easier or feasible for some substrates and harder or not possible for some other substrates. For example, it may be possible to fabricate or grow the detector, the microresonator, and the waveguides on a substrate, such as a Si substrate, but it may be difficult or not possible to grow or fabricate the light source on the same substrate. As another example, it may be possible to grow or fabricate all the system components on a III-V semiconductor substrate such as an InP or GaAs substrate.

The integration can be a hybrid integration, in which case at least some of the components are first fabricated separately and then assembled onto a common substrate. The assembly can be done by, for example, adhesively bonding the detector and the light source onto the substrate. In such a case, the microresonator and the waveguides may be monolithically integrated onto the substrate. In some cases, the bonding may require active alignment of the light source and the detector with the bus waveguides.

In certain embodiments, the common substrate is a conventional substrate used for integrated optics such as silicon dioxide that has a refractive index that is substantially lower than the materials used to make the bus waveguides and microresonators (or light sources and photodetectors). It is contemplated that the substrates may include flat, solid materials such as glass or smooth, flexible materials such as polymeric substrates. Polyester, polyacrylate and polyimide substrates, for example, may be useful in this invention. The substrate may be optically opaque or transmissive. The substrate may be polymeric, a metal, a semiconductor, or any type of glass. In one example, the substrate is silicon. As another example, the substrate may be float glass or it may be made of organic materials such as polycarbonate, acrylic, polyethylene terephthalate (PET), polyvinyl chloride (PVC), polysulfone, and the like.

To make integrated devices, typically a high index material or high index materials are deposited onto a substrate and patterned so as to form the one or more bus waveguides and the microresonator. The patterning can be done by additive methods such as vapor deposition through a mask, printing, or a lift-off process. Thermal evaporation, sputtering, printing, molecular beam epitaxy (MBE), metal organic chemical vapor deposition (MOCVD), vapor phase epitaxy (VPE), and chemical vapor deposition are all examples of methods that can be used to deposit the waveguides, microresonators, or other optical components onto the substrate. It is also possible to pattern the waveguide elements onto the substrate by subtractive methods such as etching, such as reactive ion etching or wet chemical etching. In some applications, the resonator, the optical waveguides, the light source and the detector are integrated onto the same substrate. The integrated device or parts of the integrated device can be fabricated by, for example, a molding process.

Waveguides coupled to resonators are often tapered to increase the intensity of the optical field intensity outside the waveguide, thus increasing the amount of light that couples into the microresonator. In the case of an optical fiber waveguide, the fiber may be heated and tapered or etched to a total thickness of about 1-5 μm. Likewise, with a planar or channel waveguide, the waveguide thickness may be reduced at the region where the light is coupled to the microresonator. In addition to the waveguide being reduced in size, the thickness of the cladding around the waveguide may also be reduced. Various approaches to coupling the microresonator to a waveguide or fiber are discussed in greater detail in commonly owned and co-pending U.S. Patent Published Application No. 2005-0077513, incorporated herein by reference.

There are many different examples of how a waveguide can be coupled to a microresonator resulting in a microresonator structure with an acceptable amount of optical loss and an acceptable manufacturing process. For example, FIG. 3 illustrates lateral coupling of the first bus waveguide 104 and the second bus waveguide 132 to the microresonator 118. In this configuration, the optical coupling between the waveguides 104, 132 and the microresonator 118 occurs in a sideways or lateral direction as the structure is oriented in FIG. 3. In certain embodiments, cladding is present on the outside sides 204, 232 of the waveguides 104, 132 to push the waveguide modes towards the resonator for enhanced coupling as described in, for example, commonly-owned U.S. patent application Ser. No. 11/277,769 which is incorporated herein by reference. There are many other options for configuring the cladding on the waveguides 104, 132 to accomplish coupling between the waveguides 104, 132 and the microresonator 118.

In some embodiments of a lateral coupling configuration, the waveguides 104, 132 and the microresonator 118 are fabricated using the same patterning step.

An alternative to the lateral coupling configuration of FIG. 3 is a vertical coupling configuration, an example of which is illustrated in FIG. 15. The vertically coupled optical device 1300 includes an optical microresonator 1318, a first optical waveguide 1304, and a second optical waveguide 1332 all embedded in a lower cladding layer 1305 disposed on a substrate 1303. The waveguides 1304, 1332 are surrounded by a cladding layer 1305. In a vertical coupling configuration, the optical coupling between the waveguides 1304, 1332 and the microresonator 1318 occurs in a vertical or up-and-down direction, as the optical device 1300 is oriented in FIG. 15.

In some embodiments of a vertical coupling configuration, the waveguides 1304, 1332 are patterned in a separate lithography step from the microresonator 1318.

In some embodiments, the coupling between a microresonator and a bus waveguide is an evanescent coupling, as described herein. In some other embodiments, the coupling between a microresonator and a bus waveguide is a core coupling, as discussed herein. Examples of microresonator systems where core coupling is present which may be used in connection with the present invention are described in the co-pending patent application Ser. No. 11/565,935, titled "Optical Microresonator", filed on Dec. 1, 2006 and the co-pending patent application Ser. No. 11/616,338, titled "Optical Microresonator", filed on Dec. 27, 2006, both of which were previously incorporated by reference herein.

Figure 16:
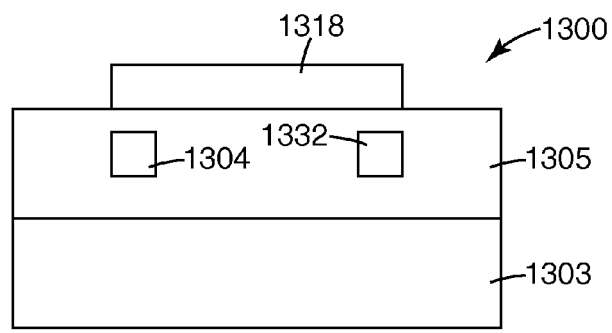
FIG. 16 is a schematic side view of an optical device with vertical coupling between two bus waveguides and a microresonator.
Figure 17:
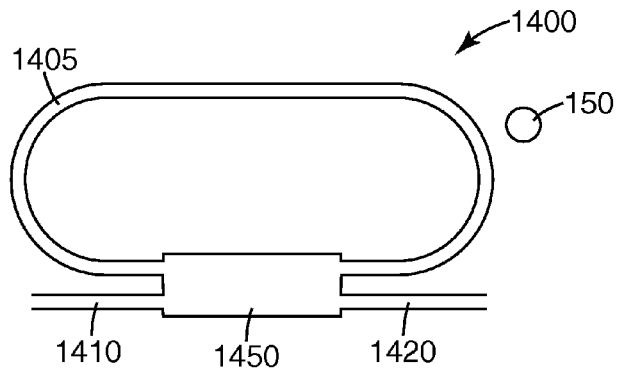
FIG. 17 is a schematic top-view of an optical system with a racetrack ring resonator coupled to two bus waveguides via a multimode interference coupler.

In some cases, the coupling between a microresonator and a bus waveguide can be carried out via a multimode interference coupler schematically illustrated in FIG. 16. Optical system 1400 includes a microresonator 1405 optically coupled to a first bus waveguide 1410 and a second bus waveguide 1420 via a multimode interference coupler (MMIC) 1450. Optical interference within the MMIC determines what fraction of light launched in waveguide 1410 couples to microresonator 1405 and what fraction couples to second bus waveguide 1420. In the exemplary optical system 1400, waveguides 1410 and 1420 are collinear. In general, the two bus waveguides may or may not be collinear.

A microdisk resonator system with two bus waveguides was numerically analyzed using an effective two dimensional finite difference time domain (FDTD) simulation to demonstrate the effect of a scattering center optically coupled to the disk microresonator system. The modeled system was similar to the system 100 illustrated in FIG. 1. In the first example, the disk diameter was 3.6 microns and the effective index of the core of the disk was 3. A water cladding having n=1.33 was assumed to be surrounding the disk resonator. Light was launched from a broadband source, having a wavelength of 1-3 microns.

Figure 18:
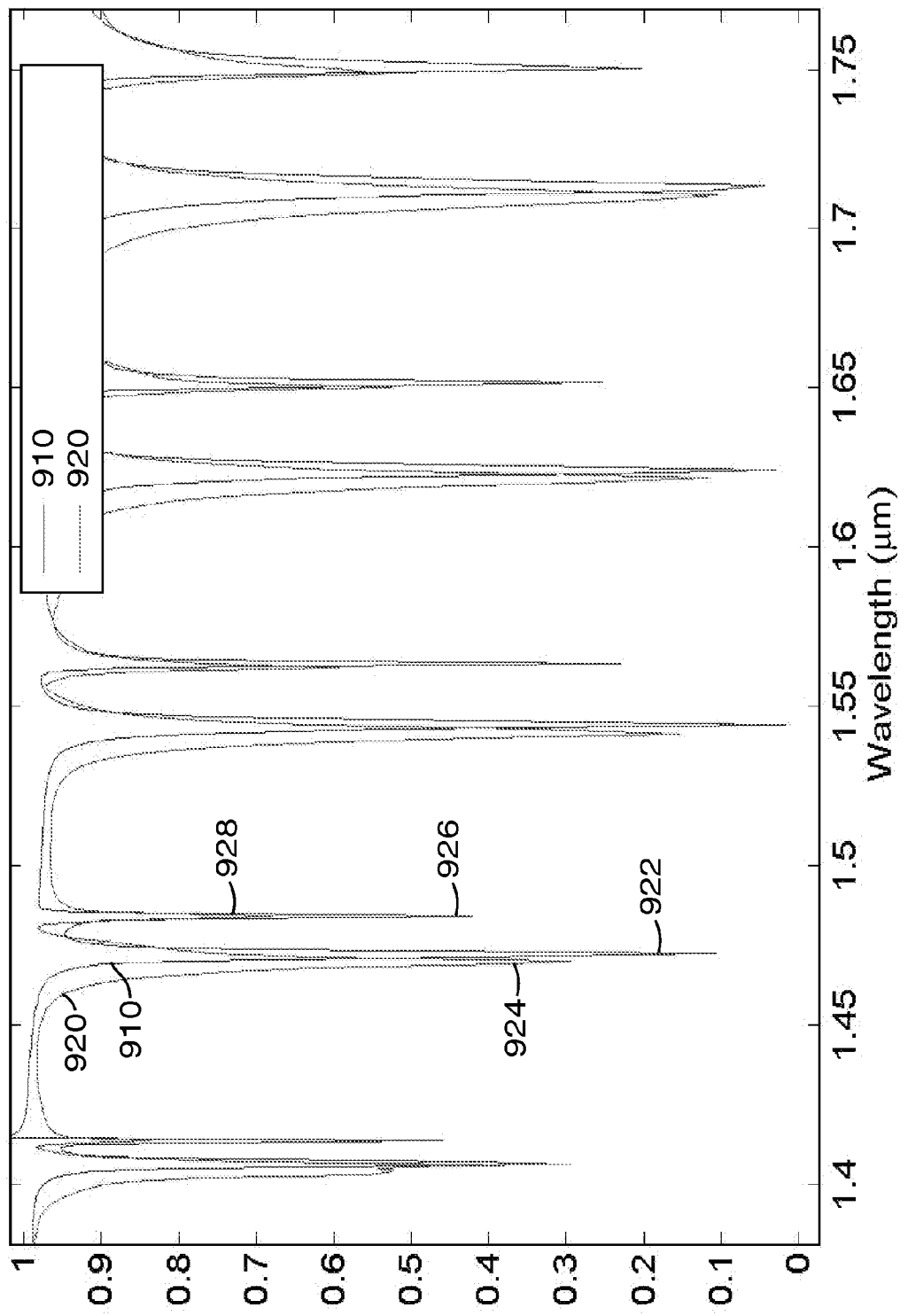
FIGS. 18 and 19 are plots of signal strength against wavelength, as detected at a through port of an optical system, with and without a gold nanoparticle scattering center, where FIG. 19 provides a higher level of detail than FIG. 18 for a portion of the plot.
Figure 19:
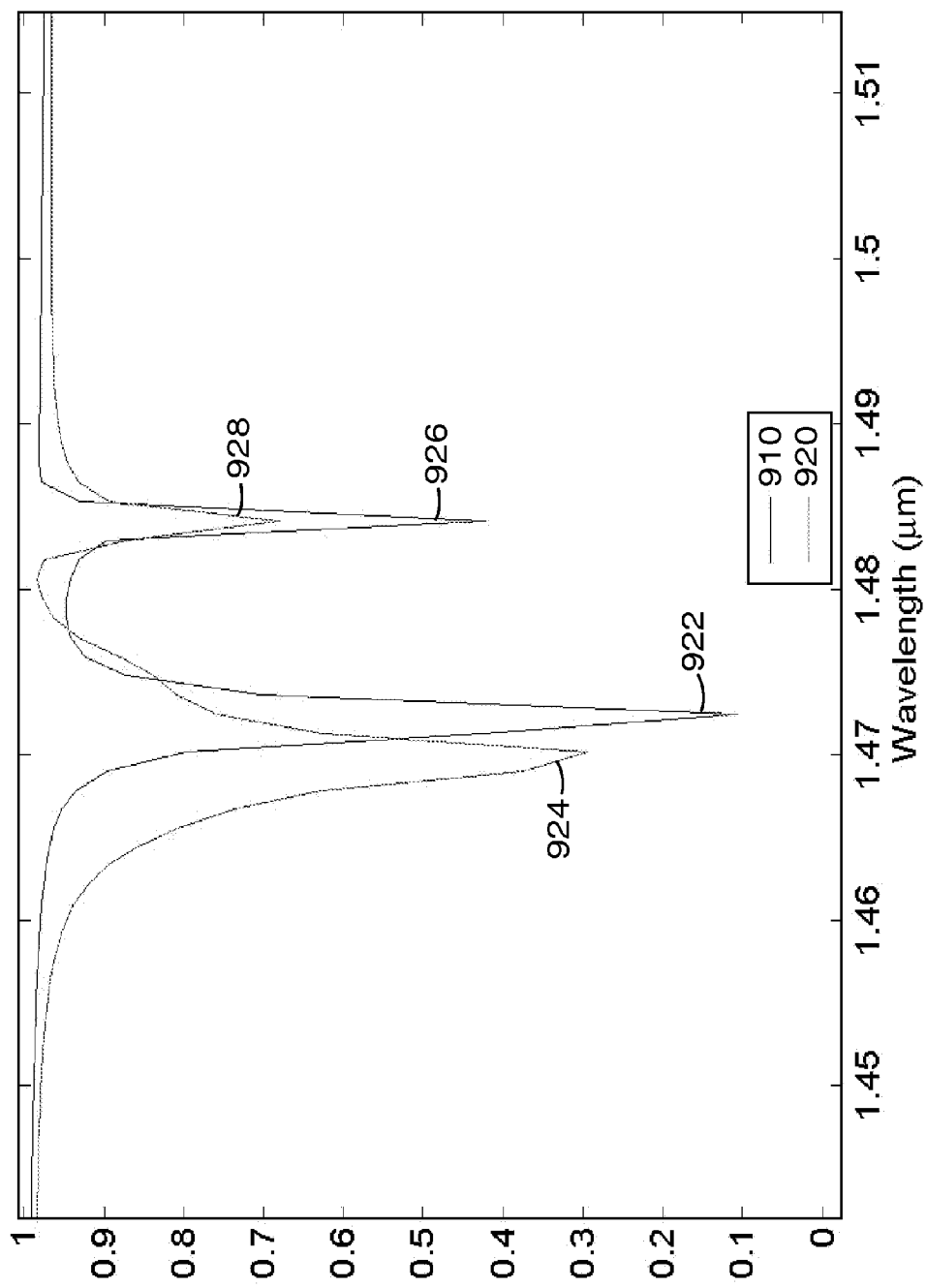

The scattering center was a gold nanoparticle having a diameter of 80 nanometers and an index of refraction of 0.54+9.58i near 1550 nanometers. The signal strength plotted against wavelength for the through port is illustrated in FIG. 18, where plot 910 represents the output for the disk with a water cladding only, and plot 920 represents the output for the disk with the gold nanoparticle in optical communication. FIG. 19 shows the same data but in greater detail for a shorter range of wavelengths. A fundamental WGM 922 near 1.5 microns is observed. The introduction of the gold nanoparticle causes the fundamental WGM 922 at 1.472 microns to be shifted by about 3 nanometers to fundamental WGM 924. The second order WGM 926 at 1.485 microns experiences a negligible shift, resulting in second order WGM 928 also at 1.485 microns after the introduction of the gold nanoparticle.

Gold has a small real refractive index and a very large imaginary refractive index (representative of absorption of the material) for visible to infrared wavelengths. Accordingly, in some cases, gold coated particles or gold particles can lead to a larger resonance wavelength shift compared to similarly sized particles of different materials.

The principle of using the spatial differences in field profiles associated with different microresonator modes to produce different responses of those modes to a perturbation was experimentally demonstrated by using the probe tip of an atomic force microscope (AFM) to simulate a perturbation due to a nanoparticle. The microresonators used in the demonstrations were disk resonators, excited by a single vertically-coupled bus waveguide.

A portable AFM (model MOBILE S, available from Nanosurf, Liestal, Switzerland) was mounted on the apparatus used for measuring the optical characteristics of microresonators via custom fixtures, allowing the AFM probe tip to contact the surface of the microresonator device while the device's optical properties were being monitored. The fixtures incorporated a 3-axis translation stage to provide coarse positioning of the AFM tip, while the piezoelectric motors of the AFM are used for fine positioning. The AFM probe tips used were commercial silicon probe tips (Model SICON A, nominal radius 10 nm available from Applied NanoStructures, Santa Clara, Calif.) that were coated with gold after obtaining the AFM from the manufacturer, resulting in a typical tip radius on the order of 100 nm. Since the refractive index of gold is much lower than air for the wavelengths used in this test (~1500 nm), each mode that encounters the probe tip will experience an effective reduction in modal effective index. Therefore, the wavelength associated with the resonance will shift to shorter wavelength (a shift to shorter wavelength will be referred to as a 'blue shift').

The procedure for spatial mapping of the resonator sensitivity is as follows. The resonators were excited using light from a high-powered erbium-doped fiber amplifier (EDFA) light source (Model NP 3000 PS, available from Nuphoton technologies, Murrieta, Calif.). An optical spectrum analyzer (OSA) (Model HP86142A available from Hewlett-Packard, Palo Alto, Calif.) is used to filter and monitor the wavelength region near a given resonance of the microresonator at the through port. The AFM probe tip is placed on or near the 'edge' of the disk resonator and is set to scan a small distance (~150 nm) periodically. The average position of the probe tip is moved radially in increments toward the center of the device (away from the edge) and the relative change in the position of the given resonance (wavelength shift induced by the probe) is recorded. After the data are collected, the wavelength shift of each resonance versus the average distance of the probe from the edge of the disk can be plotted. The resulting plot is a map of the sensitivity of the disk to a perturbation at its surface. Note that since the shift of the resonance for a given mode is expected to be directly proportional to the modal field intensity at the position of the perturbation, the sensitivity map is equivalently a map of the intensity of the fields in the resonant modes of the microresonator.

Note that since the gold-coated probe tips are quite large (about 200 nm diameter) the spatial resolution of the mapping process is limited, due to averaging over the probe size. There is also a further averaging effect from the probe tip moving about 150 nm per cycle.

Figure 20:
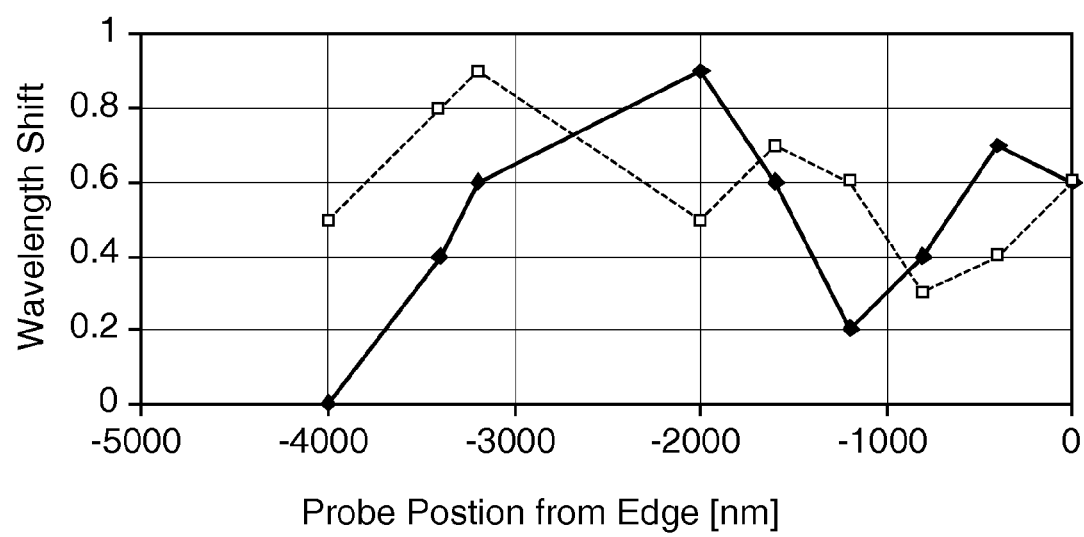
FIG. 20 is a plot of relative wavelength shift against probe position for two resonant modes of a microresonator.

In an experimental example, a radial map of the sensitivity was made on the top surface of a 100 micron diameter disk microresonator having a core of silicon nitride, with a lower cladding of silica. The average position of the tip was varied radially from near the edge of the device to approximately 4 microns from the edge of the device. Sample traces using the OSA to tune detection to wavelengths near two resonant modes were taken at 9 radial locations (plus a baseline measurement before and after) on top of the device. From these traces, the shift of each mode was determined as a function of radial position. The shifts were then normalized by dividing by a constant value for each mode, yielding a relative shift. The results are plotted in FIG. 20, plotting the relative wavelength shift against probe position for two microresonator modes.

For the 100 micron diameter resonator, two resonant modes were observed, near wavelengths of 1549.9 nm and 1551.0 nm. Based on FIG. 20 it appears that these two resonant modes are the second and third radial modes of the device, as they have two and three maxima, respectively. Furthermore, it can be appreciated that near a radial position of about 4 microns from the edge the third radial mode is affected by the presence of the AFM tip while the second is not. Also, near a radial position of about 2 microns the second radial mode is strongly affected by the presence of the AFM tip, while the third radial mode is only weakly affected. This demonstrates the differential nature of the modal response, and shows the potential for achieving self referencing by restricting the location of the perturbation. For example, if the surface of the resonator were configured so as to limit the interaction of the perturbation to a location near 4 microns in FIG. 20, the wavelength corresponding to the third radial mode could be used as a signal wavelength, whereas the wavelength corresponding to the second radial mode could be used a the reference signal.

The application also discloses sensing systems with enhanced sensitivity such as a larger wavelength shift or a stronger optical scattering between different modes. The enhanced sensitivity can allow the detection of, for example, a single analyte.

There is a need for optical sensing systems using microresonators that are easy to fabricate, produce larger spectral shifts upon exposure to analytes and can use less expensive light sources than a narrow-linewidth tunable laser.

Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An optical sensing system comprising:
   a light source;
   one or more bus waveguides comprising a first bus waveguide, the first bus waveguide comprising an input port that is in optical communication with the light source; and
   a microresonator configured so that the light source excites at least first and second resonant guided optical modes of the microresonator, the microresonator comprising:
   a first location on a surface of a core of the microresonator where a field intensity of the first mode is greater than a field intensity of the second mode, the microresonator core having a first cladding at the first location;
   a second location on a surface of the core of the microresonator where a field intensity of the first mode is less than or equal to a field intensity of the second mode, the microresonator core having a second cladding at the second location, the first cladding being different than the second cladding, wherein one of the first and second cladding is an optically-thick cladding layer, wherein a perturbation introduced at the optically-thick cladding layer will be unlikely to interact with a first or second mode of the microresonator.

2. The optical sensing system of claim 1, wherein one of the first and second cladding is a functionalized layer that is capable of chemically specific bonding with an analyte.

3. The optical sensing system of claim 1, wherein the first and second cladding have different indices of refraction.

4. An optical sensing system comprising:

a light source;

one or more bus waveguides comprising a first bus waveguide, the first bus waveguide comprising an input port that is in optical communication with the light source; and a microresonator comprising a surface, the microresonator optically coupled to the one or more bus waveguides, wherein the microresonator is configured so that the light source excites at least first and second resonant guided optical modes of the microresonator, the surface further comprising:

an unavailable first portion configured to not permit the first and second modes to interact with a perturbation of the microresonator at the unavailable first portion; and an available second portion different from the one or more coupling regions and different from the unavailable first portion, wherein the available second portion is configured to permit the first and second modes to interact with the perturbation of the microresonator in a way that the first and second resonant guided optical modes interact differently with the perturbation, wherein the microresonator surface comprises patterned cladding that prevents the perturbation from optical coupling to the unavailable first portion of the microresonator surface.

5. The system of claim 4 wherein the perturbation is one of a group consisting of:

a scattering center, and a change in refractive index of the available portion of the surface of the microresonator;

the optical sensing system further comprising a detector in optical communication with the optical sensing system.

6. The system of claim 4 wherein the perturbation is a metallic, semiconductor, dielectric or metamaterial nanoparticle.

7. The system of claim 4 wherein the microresonator and the first bus waveguide are integrated on a substrate.

8. The system of claim 4, wherein the available portion comprises a functionalized layer that is capable of chemically specific bonding with an analyte.

9. The system of claim 4, wherein the unavailable portion comprises a cladding that has a different index of refraction than an available portion.

10. The system of claim 4, wherein microresonator is optically coupled to the one or more bus waveguides at one or more respective coupling regions of the microresonator surface, wherein the unavailable portion is distinct from the one or more coupling regions.

11. A method of detecting the presence of a perturbation of a microresonator comprising:

providing an optical sensing system comprising:

a light source;

one or more bus waveguides, the one or more bus waveguides comprising a first bus waveguide that has an input port that is in optical communication with the light source; and a microresonator comprising a surface and being optically coupled to the one or more bus waveguides at one or more respective coupling regions of the surface, the microresonator being configured to support at least first and second resonant guided optical modes of the microresonator when the first and second modes are excited by the light source, the microresonator surface further comprising:

an unavailable first portion configured to not permit the first and second modes to interact with a perturbation of the microresonator at the unavailable first portion;

exciting the at least first and second resonant guided optical modes of the microresonator with the light source;

exposing an available second portion of the surface of the microresonator to a perturbation of the microresonator, wherein the available second portion is different from the unavailable first portion, the available second portion being configured to cause the perturbation to interact differently with the first and second resonant guided optical modes and detecting the interaction, wherein the microresonator surface comprises patterned cladding that prevents the perturbation from optical coupling to the unavailable first portion of the microresonator surface.

12. The method of claim 11 wherein the perturbation is one of a group consisting of:

a scattering center, and a change in refractive index of the available portion of the surface of the microresonator.

13. The method of claim 11 wherein the perturbation is a metallic, semiconductor, dielectric or metamaterial nanoparticle.

14. The method of claim 11, wherein the step of exposing induces a first frequency shift in the first resonant guided optical mode and a second frequency shift in the second resonant guided optical mode, wherein the second frequency shift can be zero; and the step of detecting the interaction further comprises comparing the first frequency shift and the second frequency shift.

15. A method of detecting the presence of a perturbation of a microresonator comprising:

providing an optical sensing system comprising:

a light source;

one or more bus waveguides, the one or more bus waveguides comprising a first bus waveguide that has an input port that is in optical communication with the light source; and a microresonator comprising a surface and being optically coupled to the one or more bus waveguides at one or more respective coupling regions of the surface, the microresonator being configured to support at least first and second resonant guided optical modes of the microresonator when the first and second modes are excited by the light source, the microresonator surface further comprising:

an unavailable first portion configured to not permit the first and second modes to interact with a perturbation of the microresonator at the unavailable first portion;

exciting the at least first and second resonant guided optical modes of the microresonator with the light source;

exposing an available second portion of the surface of the microresonator to a perturbation of the microresonator, wherein the available second portion is different from the unavailable first portion, the available second portion being configured to cause the perturbation to interact differently with the first and second resonant guided optical modes and detecting the interaction;

wherein the step of exposing induces a first frequency shift in the first resonant guided optical mode and a second frequency shift in the second resonant guided optical mode, wherein the second frequency shift can be zero; and the step of detecting the interaction further comprises comparing the first frequency shift and the second frequency shift.

* * * * *

UNITED STATES PATENT AND TRADEMARK OFFICE
CERTIFICATE OF CORRECTION

| | | |
|---|---|---|
| PATENT NO. | : 7,903,906 B2 | Page 1 of 1 |
| APPLICATION NO. | : 11/617932 | |
| DATED | : March 8, 2011 | |
| INVENTOR(S) | : Terry Lee Smith | |

It is certified that error appears in the above-identified patent and that said Letters Patent is hereby corrected as shown below:

Column 1,
Line 8, After "11/565,955," insert -- having Attorney Docket No. 62358US002, --.

Line 10, After "11/565,920," insert -- having Attorney Docket No. 62263US002, --, therefor.

Line 11, After "11/565,935," insert -- having Attorney Docket No. 62451US002, --.

Line 13, After "11/616,338," insert -- having Attorney Docket No. 62681US002, --.

Line 19, After "11/617,923" insert --, having Attorney Docket No. 62666US002, --.

Column 17,
Line 26, After ""Optical Microresonator"," insert -- having Attorney Docket No. 62451US002, --.

Line 28, After ""Optical Microresonator"," insert -- having Attorney Docket No. 62681US002, --.

Column 22,
Line 22, After ""Optical Microresonator"," insert -- having Attorney Docket No. 62451US002, --.

Line 24, After ""Optical Microresonator"," insert -- having Attorney Docket No. 62681US002, --.

Signed and Sealed this
Seventeenth Day of May, 2011

David J. Kappos
*Director of the United States Patent and Trademark Office*